(12) United States Patent
McClure et al.

(10) Patent No.: US 8,798,756 B2
(45) Date of Patent: *Aug. 5, 2014

(54) VIDEO PROCESSING UNIT FOR A VISUAL PROSTHETIC APPARATUS

(75) Inventors: Kelly H. McClure, Simi Valley, CA (US); Arup Roy, Valencia, CA (US); Richard Agustin Castro, Pasadena, CA (US); Sumit Yadav, Los Angles, CA (US); Rongqing Dai, Valencia, CA (US); Robert J. Greenberg, Los Angeles, CA (US); Da-Yu Chang, Rowland Heights, CA (US); Xiaofan Wu, Saugus, CA (US); Scott Loftin, Rosamond, CA (US); Susan McCord, Santa Monica, CA (US)

(73) Assignee: Second Sight Medical Products, Inc., Sylmar, CA (US)

(*) Notice: Subject to any disclaimer, the term of this patent is extended or adjusted under 35 U.S.C. 154(b) by 968 days.

This patent is subject to a terminal disclaimer.

(21) Appl. No.: 11/936,478

(22) Filed: Nov. 7, 2007

(65) Prior Publication Data

US 2009/0118792 A1 May 7, 2009

(51) Int. Cl.
*A61N 1/36* (2006.01)

(52) U.S. Cl.
USPC .......................................................... 607/54

(58) Field of Classification Search
CPC .......................... A61N 1/36046; A61N 1/0543
See application file for complete search history.

(56) References Cited

U.S. PATENT DOCUMENTS

| 5,109,844 | A | | 5/1992 | de Juan, Jr. et al. | |
|---|---|---|---|---|---|
| 5,845,136 | A | * | 12/1998 | Babcock | 713/300 |
| 5,935,155 | A | | 8/1999 | Humayun et al. | |
| 5,944,747 | A | | 8/1999 | Greenberg et al. | |
| 6,400,989 | B1 | | 6/2002 | Eckmiller | |
| 6,458,157 | B1 | | 10/2002 | Suaning | |
| 6,570,385 | B1 | * | 5/2003 | Roberts et al. | 324/378 |
| 6,718,209 | B2 | | 4/2004 | Williamson et al. | |
| 6,974,533 | B2 | | 12/2005 | Zhou | |
| 7,974,699 | B2 | * | 7/2011 | Tano et al. | 607/54 |
| 2003/0065370 | A1 | * | 4/2003 | Lebel et al. | 607/60 |
| 2005/0222624 | A1 | | 10/2005 | Greenberg et al. | |
| 2006/0003809 | A1 | * | 1/2006 | Boling et al. | 455/564 |
| 2006/0058857 | A1 | | 3/2006 | Tano et al. | |
| 2006/0220897 | A1 | * | 10/2006 | Cheng | 340/815.4 |
| 2007/0073389 | A1 | * | 3/2007 | Bolduc et al. | 623/1.36 |
| 2009/0073950 | A1 | * | 3/2009 | Guccione et al. | 370/341 |

FOREIGN PATENT DOCUMENTS

| GB | 2 019 625 | 10/1979 |
|---|---|---|
| WO | WO 96/01665 | 1/1996 |
| WO | WO 2007/064916 | 6/2007 |

* cited by examiner

*Primary Examiner* — Paula J Stice
(74) *Attorney, Agent, or Firm* — Scott B. Dunbar; Alessandro Steinfl

(57) ABSTRACT

A video processing unit configured to convert a video image to stimulation patterns for stimulating neural tissue in a subject's eye and comprising a power button, wherein the video processing unit is configured to be powered on after a first time interval upon activation of a power button, wherein the video processing unit is configured to be powered off after a second time interval upon activation of a power button.

11 Claims, 24 Drawing Sheets

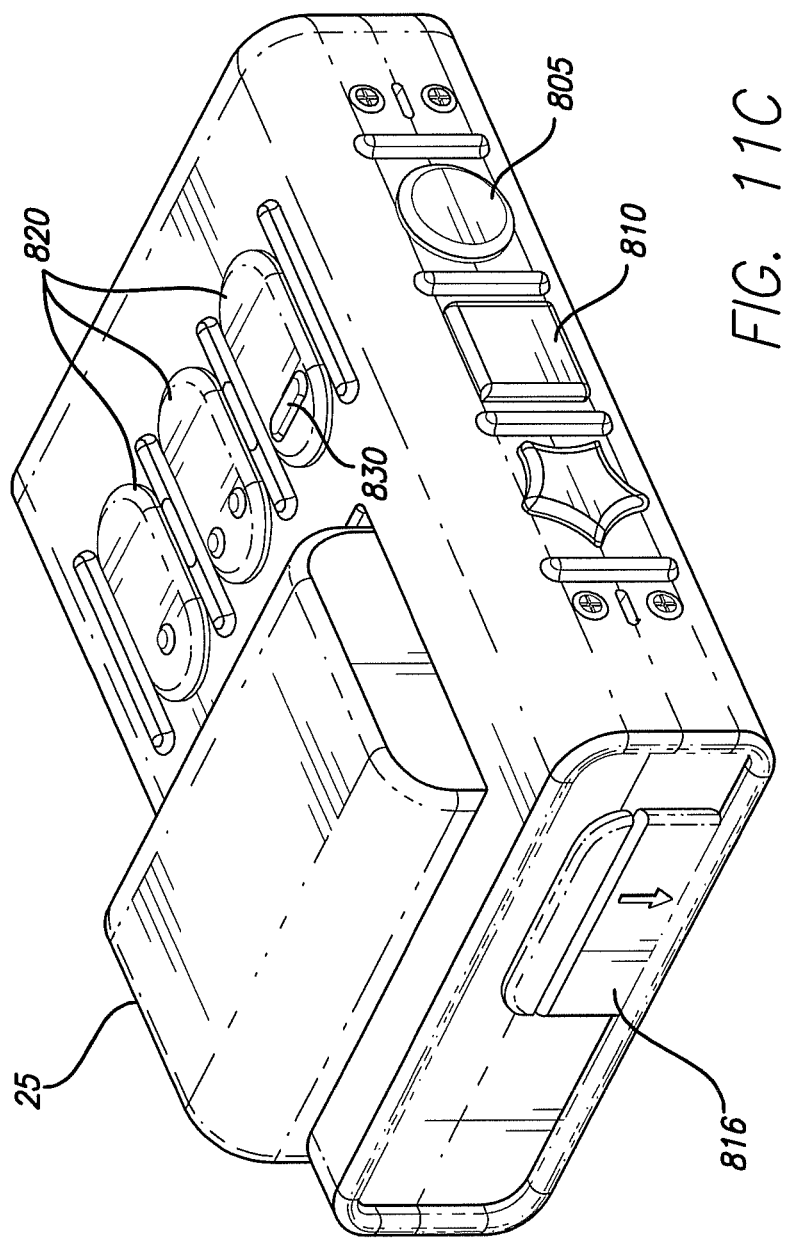

VIDEO PROCESSING UNIT FOR A VISUAL PROSTHETIC APPARATUS

FEDERALLY SPONSORED RESEARCH OR DEVELOPMENT

The present invention was made with support from the United States Government under Grant number R24EY12893-01, awarded by the National Institutes of Health. The United States Government has certain rights in the invention.

CROSS REFERENCE TO RELATED APPLICATIONS

This application claims the benefit of U.S. Design patent application Ser. No. 29/291,134, filed Aug. 15, 2007 for "Video Processing Unit For Prosthetic Apparatus", the disclosure of which is incorporated herein by reference in its entirety. This application claims the benefit of to U.S. patent application Ser. No. 11/881,433, filed Jul. 27, 2007 for "Visual Prosthesis", the disclosure of which is incorporated herein by reference in its entirety. This application claims priority to PCT application No. PCT/US2007/013918 for "Apparatus and Method for Electrical Stimulation of Human Retina" filed on Jun. 15, 2007, which is incorporated herein by reference in its entirety.

FIELD

The present disclosure relates to visual prostheses configured to provide neutral stimulation for the creation of artificial vision.

BACKGROUND

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising a prosthesis for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparatuses to aid the visually impaired. Specifically, great effort has been expended in the area of intraocular visual prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretial). This placement must be mechanically stable, minimize the distance between the device electrodes and the visual neurons, and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Opthalmol. 272 (1985). These retinal tacks have proved to be biocompatible and remain embedded in the retina, and choroid/sclera, effectively pinning the retina against the choroid and the posterior aspects of the globe.

Retinal tacks are one way to attach a retinal array to the retina. U.S. Pat. No. 5,109,844 to de Juan describes a flat electrode array placed against the retina for visual stimulation. U.S. Pat. No. 5,935,155 to Humayun describes a visual prosthesis for use with the flat retinal array described in de Juan.

SUMMARY

According to a first aspect, a visual prosthesis apparatus is disclosed, a visual prosthesis apparatus comprising: a video capture device for capturing a video image; a video processing unit associated with the video capture device, the video processing unit configured to convert the video image to stimulation patterns; and a retinal stimulation system configured to stimulate neural tissue in a subject's eye based on the stimulation patterns, wherein the video processing unit is configured to be powered on after a first time interval upon activation of a power button, wherein the video processing unit is configured to be powered off after a second time interval upon activation of a power button.

According to a second aspect, a visual prosthesis apparatus is disclosed, a visual prosthesis apparatus comprising: a video capture device for capturing a video image; a video processing unit associated with the video capture device, the video processing unit comprising a video processor for converting the video image to a digital video stream; a memory for storing the digital video stream; a video preprocessor data interface for forming stimulation patterns based on the stored digital video stream; and a retinal stimulation system configured to stimulate neural tissue in a subject's eye based on the stimulation patterns.

According to a third aspect, a video processing unit is disclosed, the video processing unit configured to convert a video image to stimulation patterns for stimulating neural tissue in a subject's eye and comprising a power button, wherein the video processing unit is configured to be powered on after a first time interval upon activation of a power button, wherein the video processing unit is configured to be powered off after a second time interval upon activation of a power button.

According to a fourth aspect, a video processing unit configured to convert a video image to stimulation patterns for stimulating neural tissue in a subject's eye is disclosed, the video processing unit comprising a video processor for converting a video image to a digital video stream; a memory for storing the digital video stream; and a video preprocessor data interface for forming stimulation patterns based on the stored digital video stream.

According to a fifth aspect, a method for providing artificial vision is disclosed, the method comprising powering a video processing unit a first amount of time after a power button is activated; capturing a video image; converting the video image to stimulation patterns using the video processing unit; and stimulating neural tissue in a subject's eye based on the stimulation patterns.

According to a sixth aspect, a method for providing artificial vision is disclosed, the method comprising capturing a video image; converting the video image to a digital video stream; storing the digital video stream; forming stimulation patterns based on the stored digital video stream; and stimulating neural tissue in a subject's eye based on the stimulation patterns.

According to a seventh aspect, a visual prosthesis apparatus is disclosed, the visual prosthesis apparatus comprising: a video capture device for capturing a video image; a video processing unit associated with the video capture device, the video processing unit configured to convert the video image to stimulation patterns; and a retinal stimulation system configured to stimulate neural tissue in a subject's eye based on the stimulation patterns, wherein the video processing unit is configured to be powered on after a first time interval upon activation of a power button, wherein the video processing unit is configured to be powered off after a second time interval upon activation of a power button, wherein the video processing unit is disposed on a visor.

According to a eight aspect, a visual prosthesis apparatus is disclosed, the video prosthesis apparatus comprising a video capture device for capturing a video image; a video processing unit associated with the video capture device, the video processing unit comprising a video processor for converting the video image to a digital video stream; a memory for storing the digital video stream; a video preprocessor data interface for forming stimulation patterns based on the stored digital video stream; and a retinal stimulation system configured to stimulate neural tissue in a subject's eye based on the stimulation patterns, wherein the video processing unit is disposed on a visor.

According to a ninth aspect, a video processing unit is disclosed, the video processing unit configured to convert a video image to stimulation patterns for stimulating neural tissue in a subject's eye and comprising a power button, wherein the video processing unit is configured to be powered on after a first time interval upon activation of a power button, wherein the video processing unit is configured to be powered off after a second time interval upon activation of a power button, wherein the video processing unit is disposed on a visor.

Further embodiments are shown in the specification, drawings and claims of the present application.

BRIEF DESCRIPTION OF THE FIGURES

FIGS. 11A-G and 12 show the video processing unit already briefly shown with reference to FIGS. 9 and 10.

FIGS. 13-1, 13-2, 13-3 and 13-4 show an exemplary embodiment of a video processing unit. FIG. 13-1 should be viewed at the left of FIG. 13-2. FIG. 13-3 should be viewed at the left of FIG. 13-4. FIGS. 13-1 and 13-2 should be viewed on top of FIGS. 13-3 and 13-4.

FIGS. 14-1, 14-2, 14-3 and 14-4 show another exemplary embodiment of a video processing unit. FIG. 14-1 should be viewed at the left of FIG. 14-2. FIG. 14-3 should be viewed at the left of FIG. 14-4. FIGS. 14-1 and 14-2 should be viewed on top of FIGS. 14-3 and 14-4.

In the following description, like reference numbers are used to identify like elements. Furthermore, the drawings are intended to illustrate major features of exemplary embodiments in a diagrammatic manner. The drawings are not intended to depict every feature of every implementation nor relative dimensions of the depicted elements, and are not drawn to scale.

DETAILED DESCRIPTION

The present disclosure is concerned with a visual apparatus and a method for creation of artificial vision. In particular, the present disclosure provides an interface and method for controlling a visual prosthesis (i.e. device) implanted in an individual patient (i.e. subject) to create artificial vision.

Figure 1:
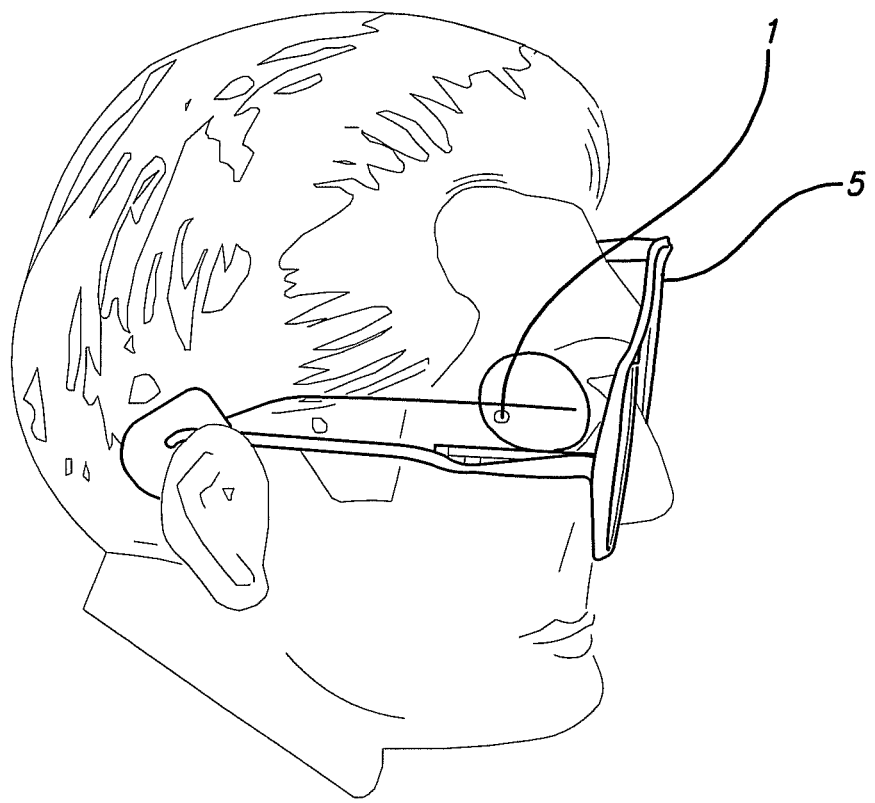
FIG. 1 shows a visual prosthesis apparatus according to the present disclosure.

FIG. 1 shows a visual prosthesis apparatus. The visual apparatus comprises, in combination, an implantable retinal stimulation system 1 and a video capture/transmission apparatus or visor embodied in visor/Glasses 5. An exemplary retinal stimulation system 1 is shown in more detail in FIGS. 2-5 and an exemplary visor 5 is shown in more detail in FIGS. 6 and 7.

The retinal stimulation system 1 is further disclosed in U.S. application Ser. No. 11/207,644, filed Aug. 19, 2005 for "Flexible Circuit Electrode Array" by Robert J. Greenberg, et, al. incorporated herein by reference, and is intended for use in subjects with retinitis pigmentosa. The visor 5 is further disclosed in International Patent Application No. PCT/US07/13918, filed on Jun. 14, 2007 and entitled "APPARATUS AND METHOD FOR ELECTRICAL STIMULATION OF HUMAN RETINA," also incorporated herein by reference.

Figure 2:
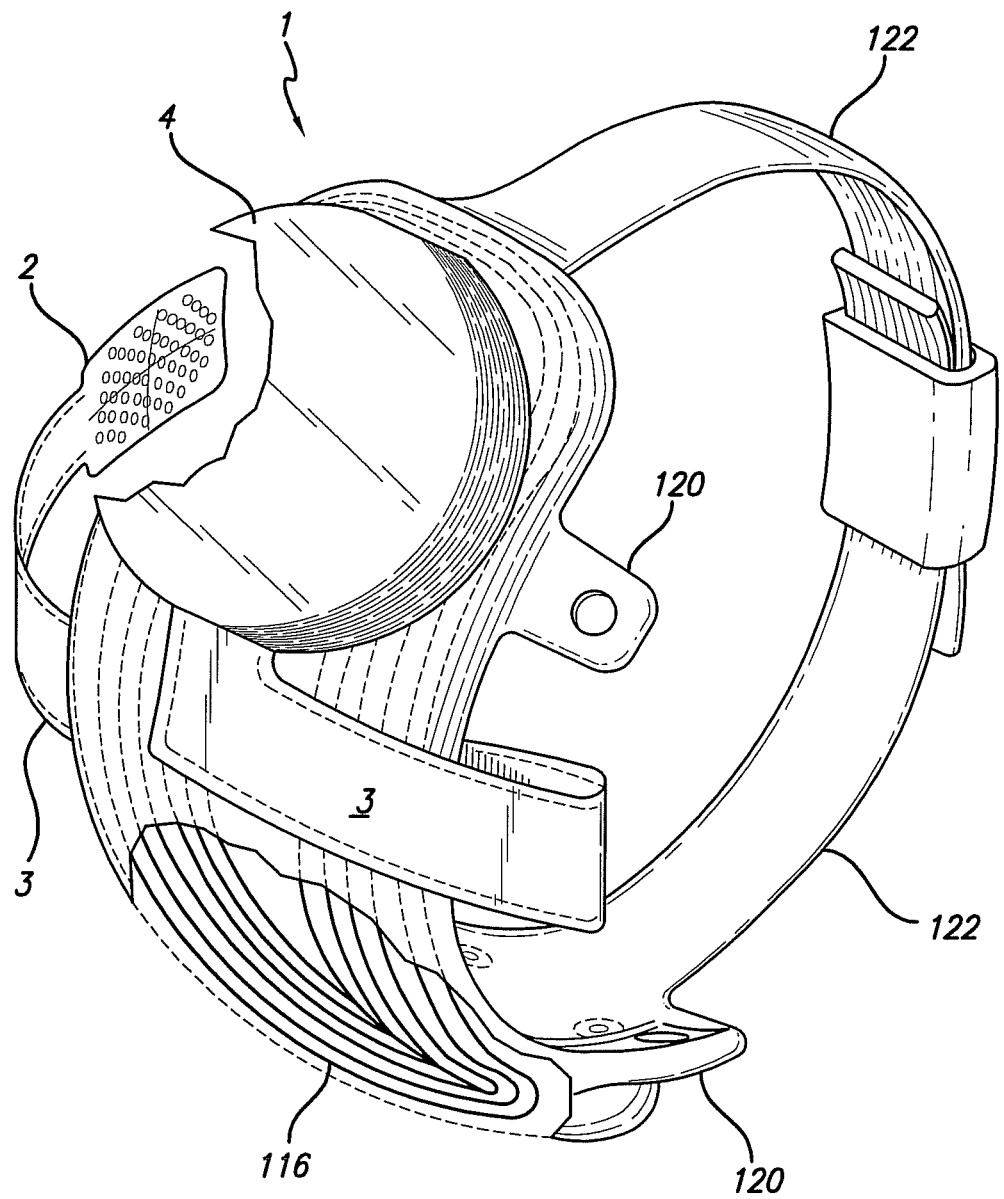
FIGS. 2 and 3 show a retinal stimulation system adapted to be implanted into a subject.
Figure 3:
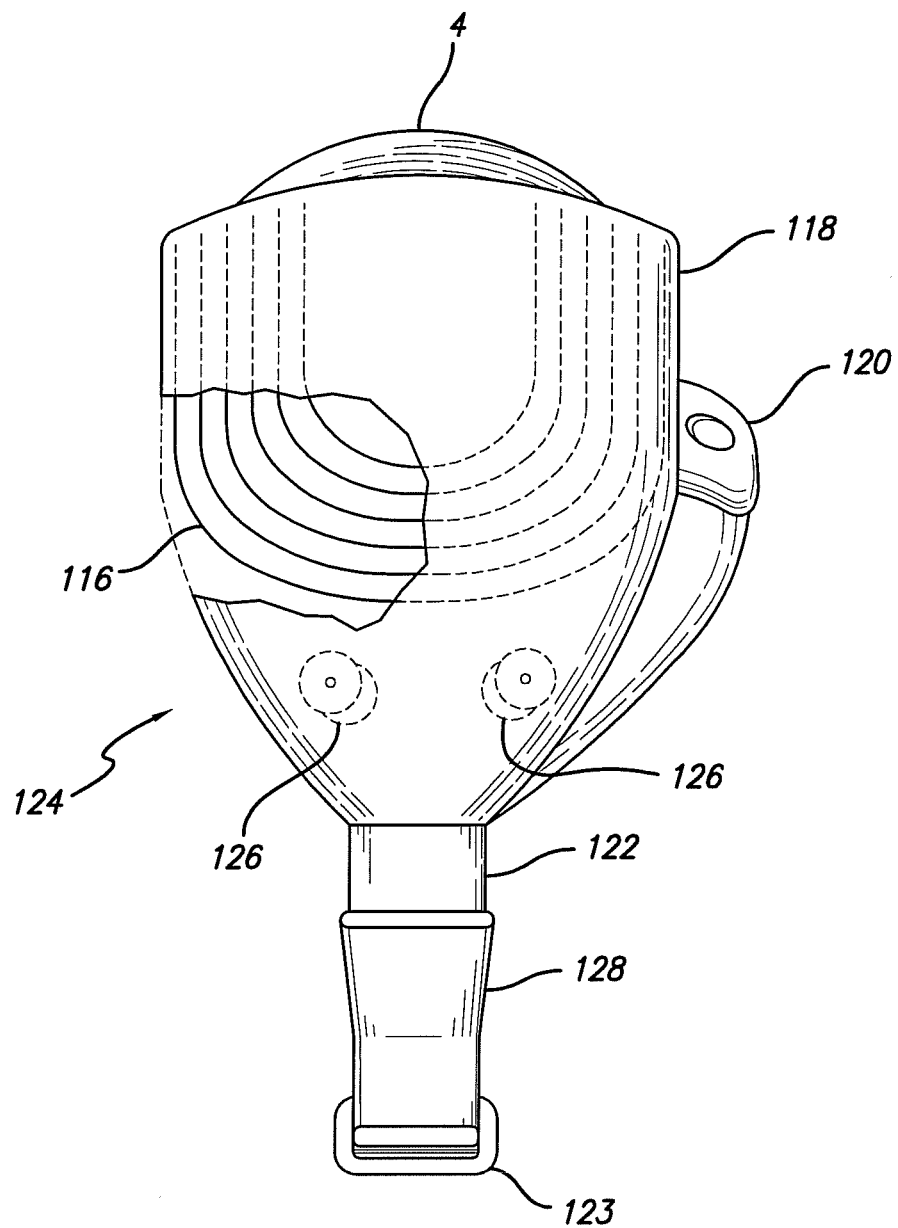

The exemplary retinal stimulation system 1, shown in FIGS. 2 and 3, is an implantable electronic device containing an inductive coil 116 and an electrode array 2 that is electrically coupled by a cable 3 that pierces sclera of the subject's eye to an electronics package 4, external to the sclera. The retinal stimulation system 1 is designed, for example, to elicit visual percepts in blind subjects with retinitis pigmentosa.

Human vision provides a field of view that is wider than it is high. This is partially due to fact that we have two eyes, but even a single eye provides a field of view that is approximately 90° high and 140° to 160° degrees wide. It is therefore, advantageous to provide a flexible circuit electrode array 2 that is wider than it is tall. This is equally applicable to a cortical visual array. In which case, the wider dimension is not horizontal on the visual cortex, but corresponds to horizontal in the visual scene.

Figure 8:
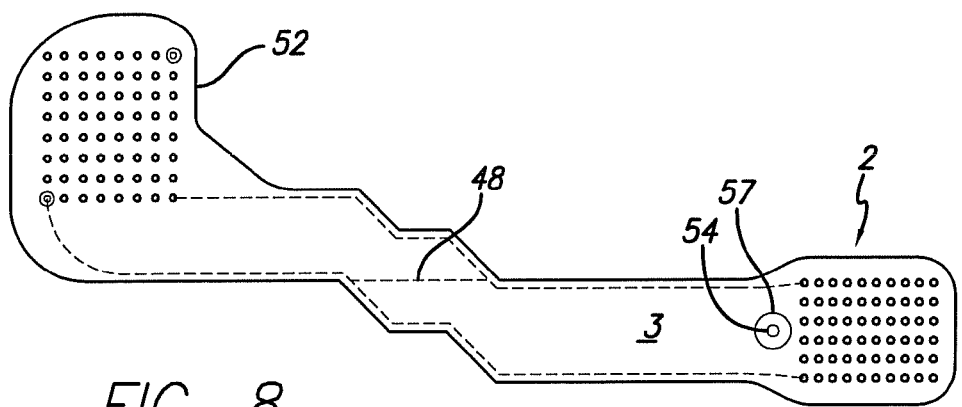
FIG. 8 shows a flexible circuit electrode array, also shown in FIG. 2.

FIG. 8 shows the flexible circuit electrode array 2 prior to folding and attaching to the electronics package 4 of FIG. 2. At one end of the flexible circuit cable 3 is an interconnection pad 52 for connection to the electronics package 4. At the other end of the flexible circuit cable 3 is the flexible circuit electrode array 2. Further, an attachment point 54 may be provided near the flexible circuit electrode array 2. A retina tack (not shown) is placed through the attachment point 54 to hold the flexible circuit electrode array 2 to the retina. A stress relief 57 may be provided surrounding the attachment point 54. The stress relief 57 may be made of a softer polymer than the flexible circuit, or it may include cutouts or thinning of the polymer to reduce the stress transmitted from the retina tack to the flexible circuit electrode array 2. The flexible circuit cable 3 may be formed in a dog leg pattern so than when it is folded at fold 48 it effectively forms a straight flexible circuit cable 3 with a narrower portion at the fold 48 for passing through the sclerotomy. The electrode array 2 may comprise a polyimide cable that houses wire conductors and an array of exposed platinum electrodes in a grid. In one embodiment, there are sixty electrodes arranged in a 6×10 grid.

The electronics package 4 of FIGS. 2 and 3 can be electrically coupled to the inductive coil 116. In one aspect, the inductive coil 116 contains a receiver and transmitter antennae made from wound wire. Alternatively, the inductive coil 116 may be made from a thin film polymer sandwich with wire traces deposited between layers of thin film polymer. The electronics package 4 may contain components and an Application Specific Integrated Circuit (ASIC) for processing the received data and using the received power to generate the required stimulation output. The electronics package 4 and the inductive coil 116 may be held together by a molded body 118 shown in FIG. 3. As also shown in FIG. 3, the molded body 118 may also include suture tabs 120 shown in FIG. 3. The molded body narrows to form a strap 122 which surrounds the sclera and holds the molded body 118, inductive coil 116, and electronics package 4 in place. The molded body 118, suture tabs 120 and strap 122 are preferably an integrated unit made of silicone elastomer. Silicone elastomer can be formed in a pre-curved shape to match the curvature of a typical sclera. Furthermore, silicone remains flexible enough to accommodate implantation and to adapt to variations in the curvature of an individual sclera. In one aspect, the inductive coil 116 and molded body 118 are oval shaped, and in this way, a strap 122 can better support the oval shaped coil.

The eye moves constantly. The eye moves to scan a scene and also has a jitter motion to prevent image stabilization. Even though such motion is useless in the blind, it often continues long after a person has lost their sight. Thus, in one embodiment of the present disclosure, the entire retinal stimulation system 1 of the prosthesis is attached to and supported by the sclera of a subject. By placing the device under the rectus muscles with the electronics package in an area of fatty tissue between the rectus muscles, eye motion does not cause any flexing which might fatigue, and eventually damage, the device.

FIG. 3 shows a side view of the retinal stimulation system 1, in particular, emphasizing the fan tail 124. When the retinal prosthesis is implanted, the strap 122 is passed under the eye muscles to surround the sclera. The inductive coil 116 and molded body 118 should also follow the strap under the lateral rectus muscle on the side of the sclera. The retinal stimulation system 1 of the visual prosthesis apparatus is very delicate. It is easy to tear the molded body 118 or break wires in the inductive coil 116. In order to allow the molded body 118 to slide smoothly under the lateral rectus muscle, the molded body is shaped in the form of a fan tail 124 on the end opposite the electronics package 4. Element 123 shows a retention sleeve, while elements 126 and 128 show holes for surgical positioning and a ramp for surgical positioning, respectively.

Figure 4:
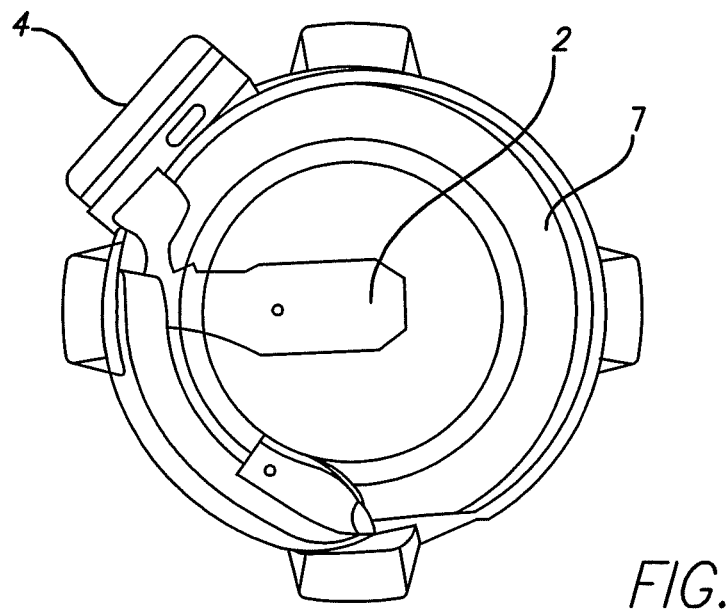
FIG. 4 shows a front view of the implanted retinal stimulation system.
Figure 5:
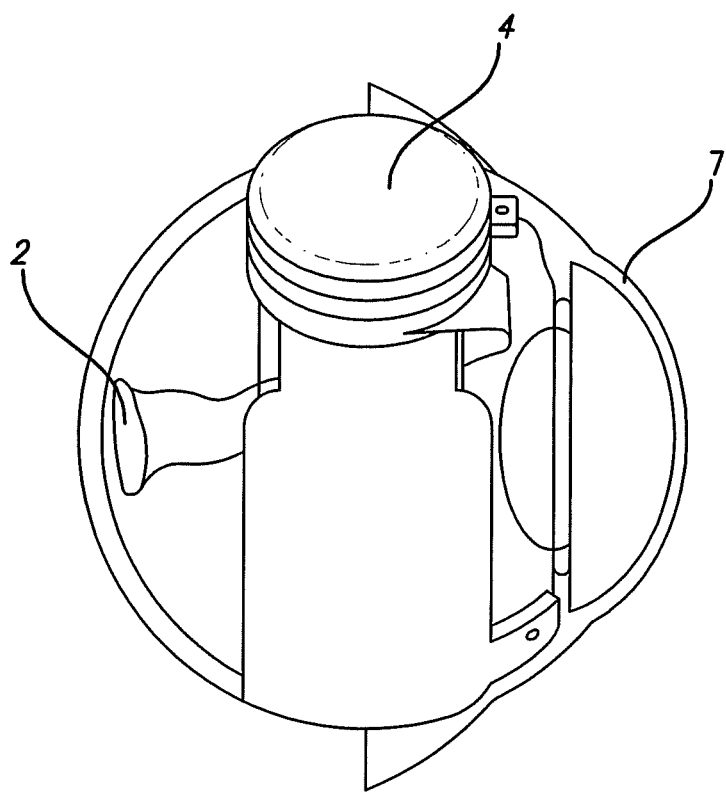
FIG. 5 shows a side view of the implanted system of FIG. 9.

FIGS. 4 and 5 show front and side views of the Retinal stimulation system 1 implanted with respect to the subject's eye 7. As shown in FIGS. 4 and 5, the electrode array 2 enters the eye through a pars plana incision and is placed on the retina over the fovea using a retinal tack. The remaining Retinal stimulation system 1 is secured to the eye by means of a scleral band held in place by a Watzke sleeve (typical of scleral procedures), and also by suture tabs. Additionally, another suture may be placed around the scleral band in the inferior medical quadrant of the eye.

Figure 6A:
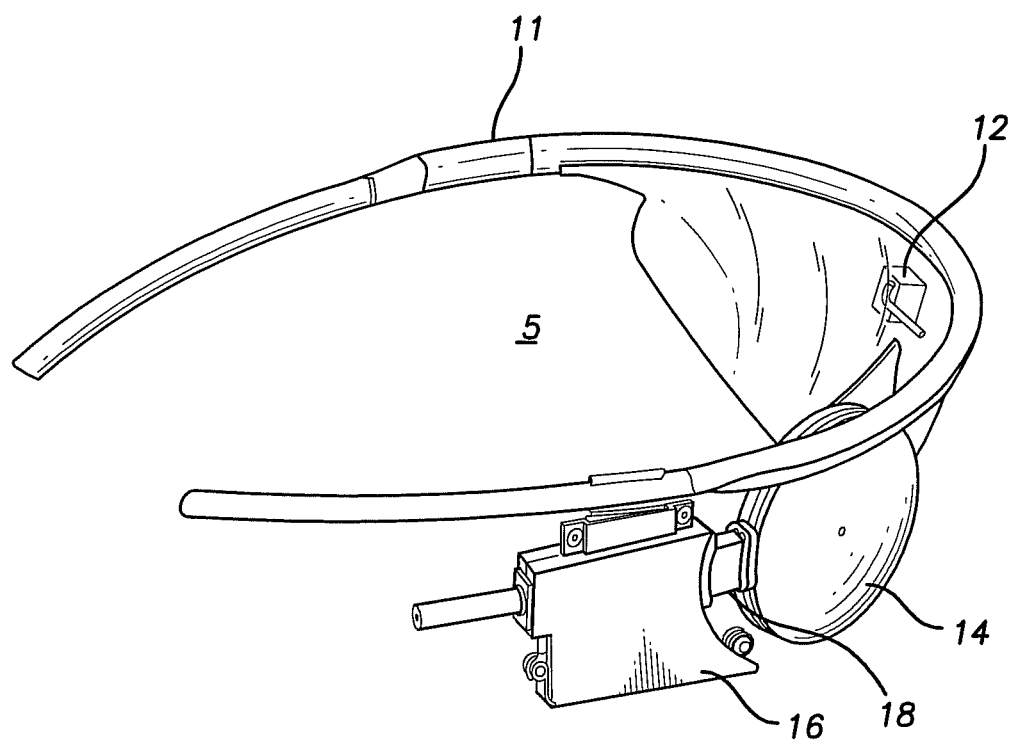
FIGS. 6A and 7 show a video capture/transmission apparatus or visor adapted to be used in combination with the retinal stimulation system of FIGS. 2-5.
Figure 7:
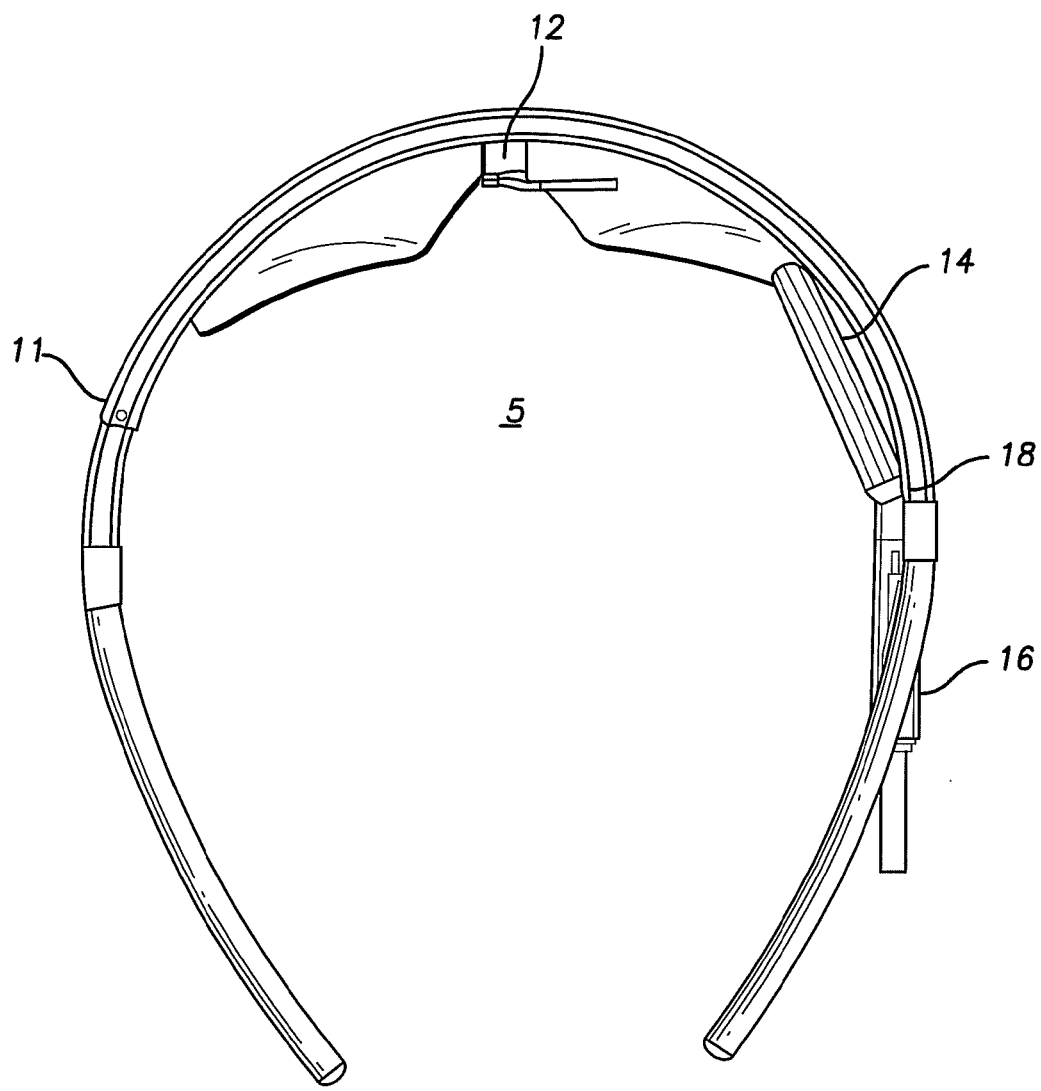

Referring to FIGS. 6A and 7, the glasses 5 may comprise, for example, a frame 11 holding a camera 12, an external coil 14 and a mounting system 16 for the external coil 14. The mounting system 16 may also enclose the RF circuitry. In this configuration, the video camera 12 captures live video. The video signal is sent to an external Video Processing Unit (VPU) 20 (shown in FIGS. 9-12 and discussed below), which processes the video signal and subsequently transforms the processed video signal into electrical stimulation patterns or data. The electrical stimulation data are then sent to the external coil 14 that sends both data and power via radio-frequency (RF) telemetry to the coil 116 of the retinal stimulation system 1, shown in FIGS. 2 and 3. The coil 116 receives the RF commands which control the application specific integrated circuit (ASIC) which in turn delivers stimulation to the retina of the subject via a thin film electrode array (TFEA). In one aspect of an embodiment, light amplitude is recorded by the camera 12. The VPU 20 may use a logarithmic encoding scheme to convert the incoming light amplitudes into the electrical stimulation patterns or data. These electrical stimulation patterns or data may then be passed on to the Retinal Stimulation System 1, which results in the retinal cells being stimulated via the electrodes in the electrode array 2 (shown in FIGS. 2, 3 and 8). In one exemplary embodiment, the electrical stimulation patterns or data being transmitted by the external coil 14 is binary data. The external coil 14 may contain a receiver and transmitter antennae and a radio-frequency (RF) electronics card for communicating with the internal coil 116.

Figure 6B:
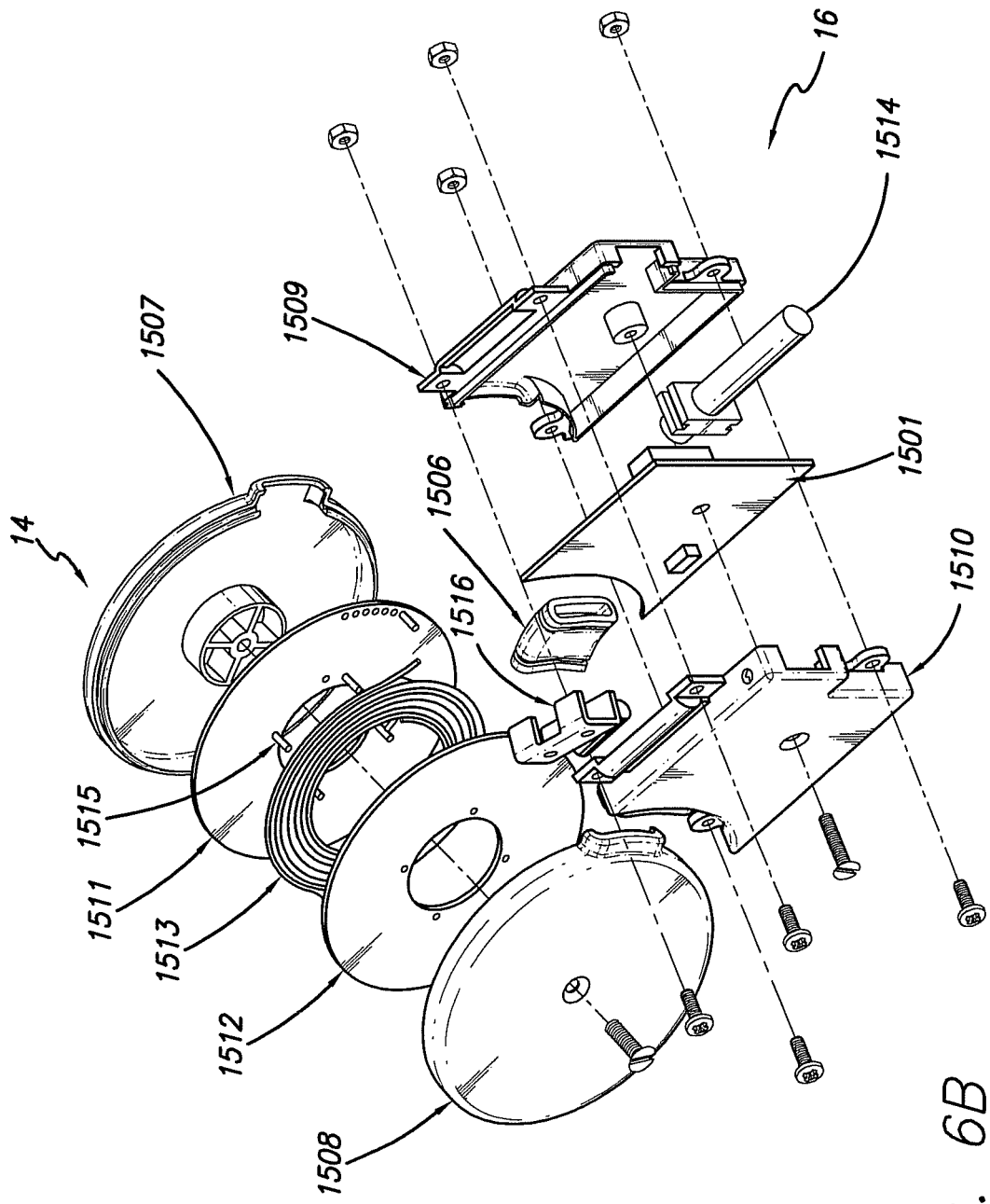
FIG. 6B shows exploded view of the external coil arrangement and mounting system shown in FIGS. 6A and 7.
Figure 12:
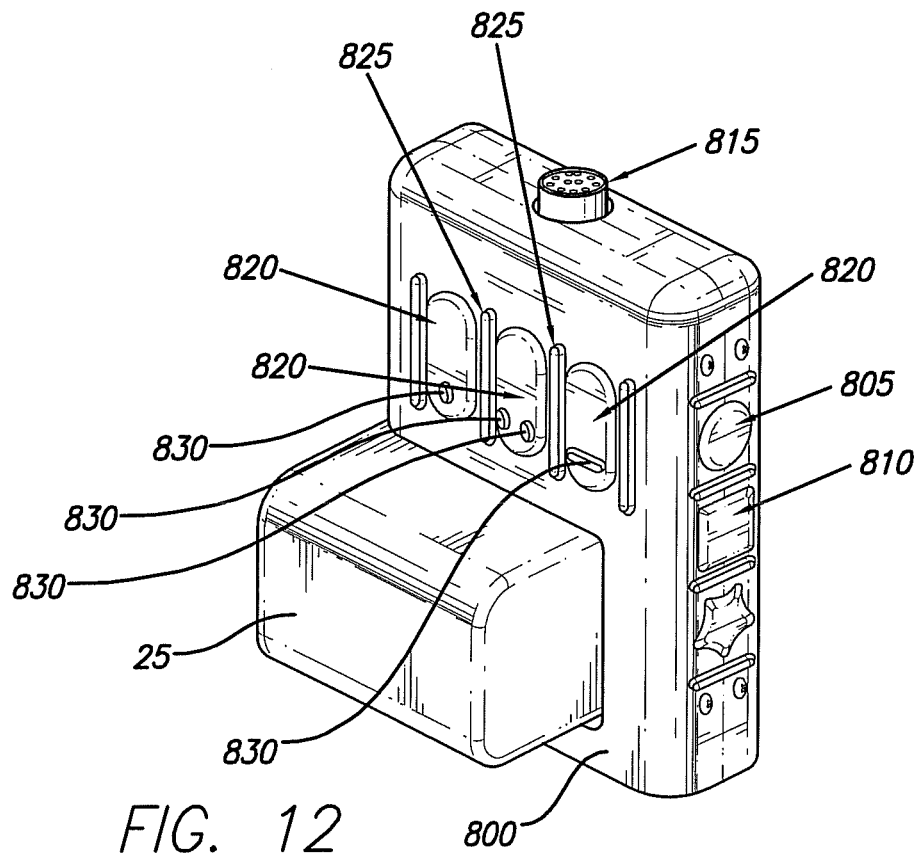
Figures 1, 13:
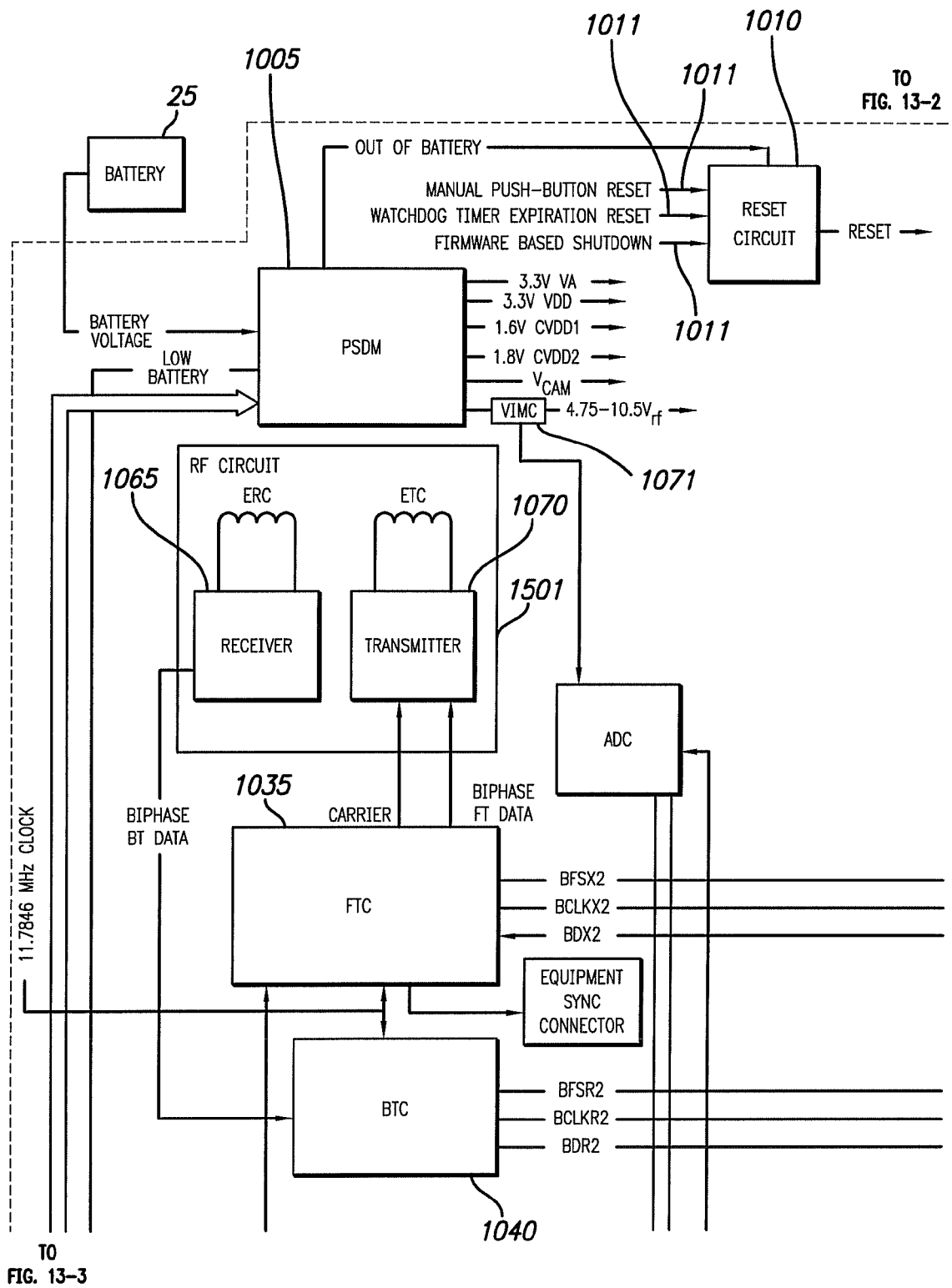
Figures 2, 13:
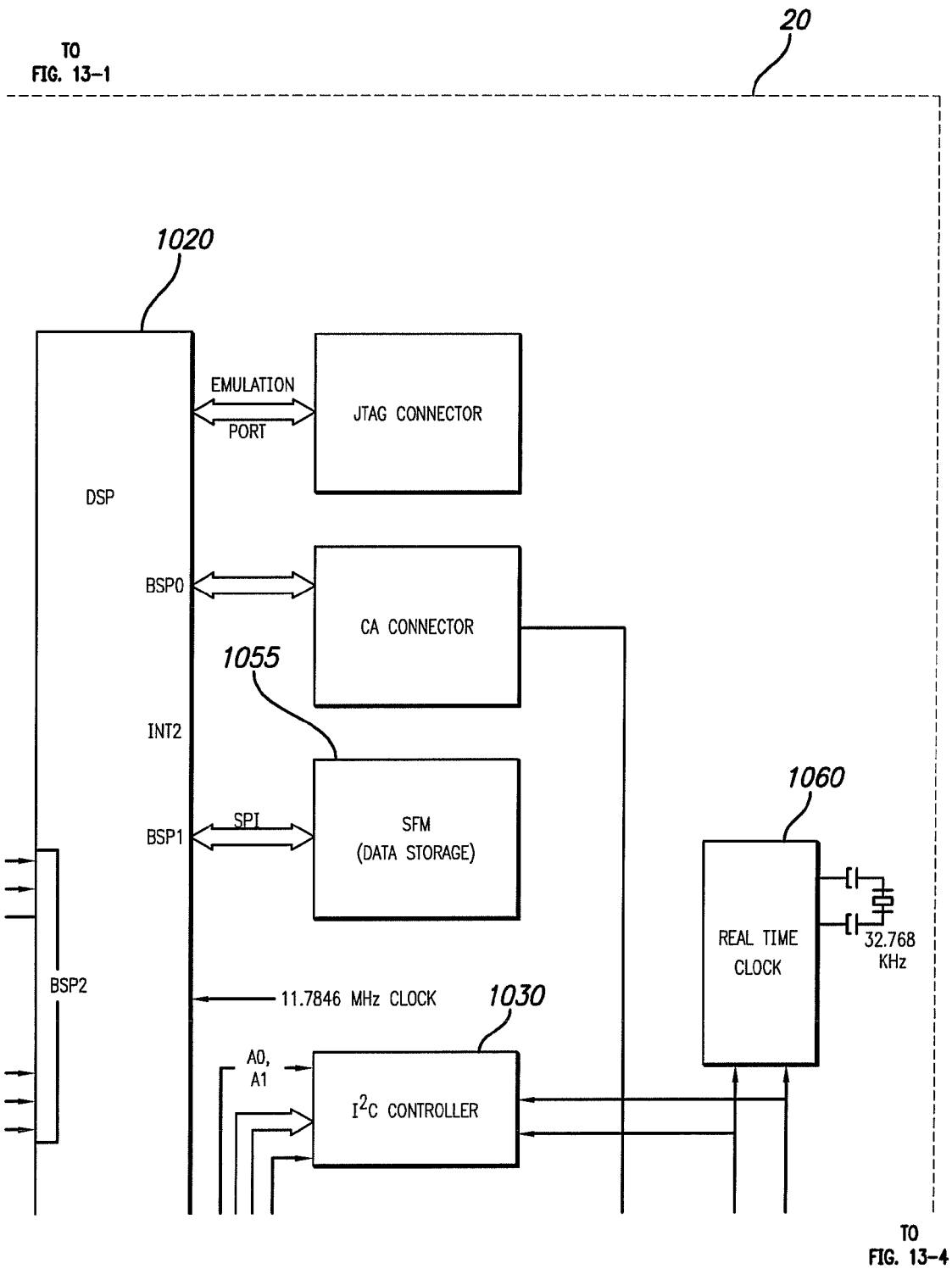
Figures 3, 13:
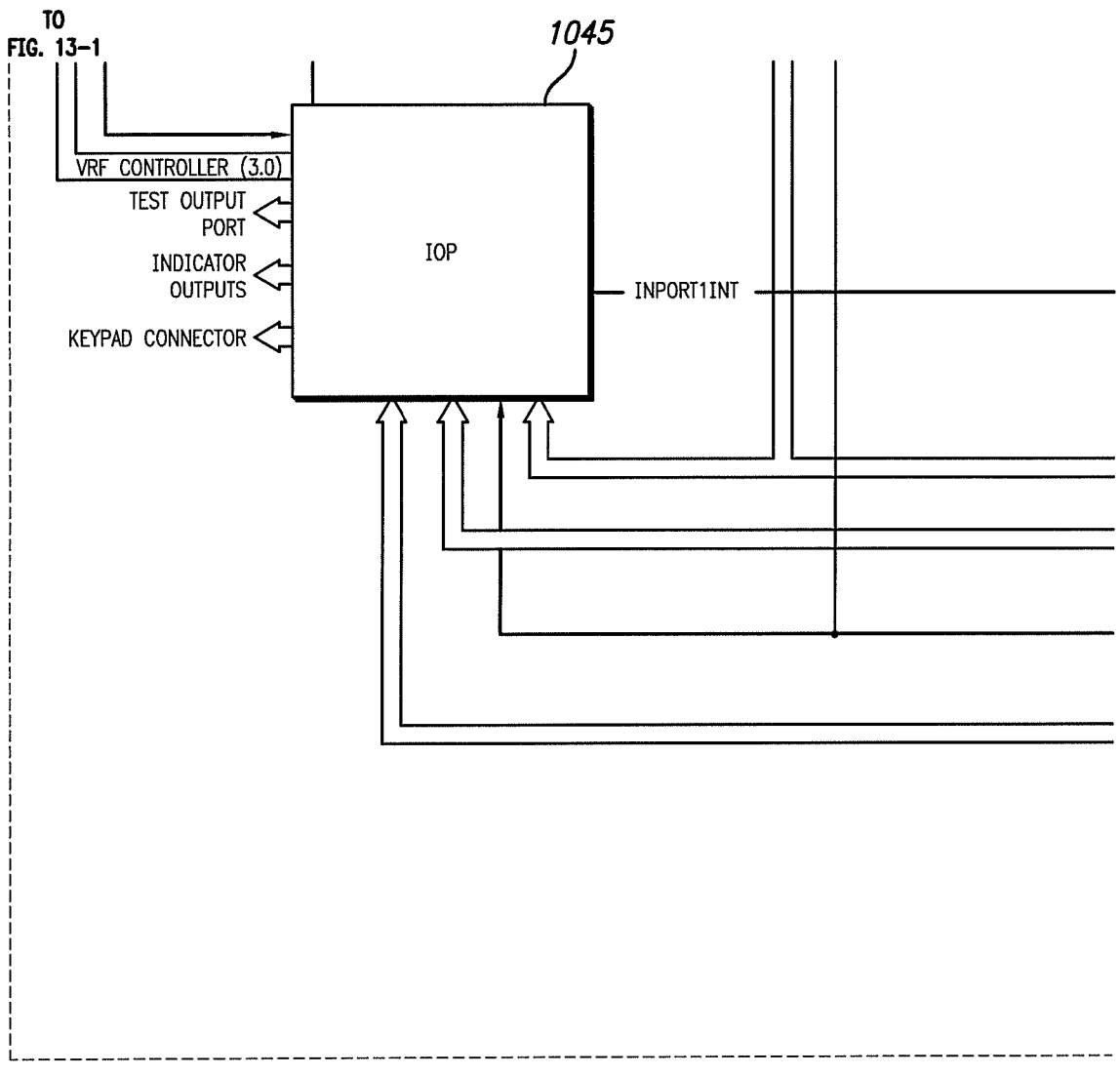
Figures 4, 13:
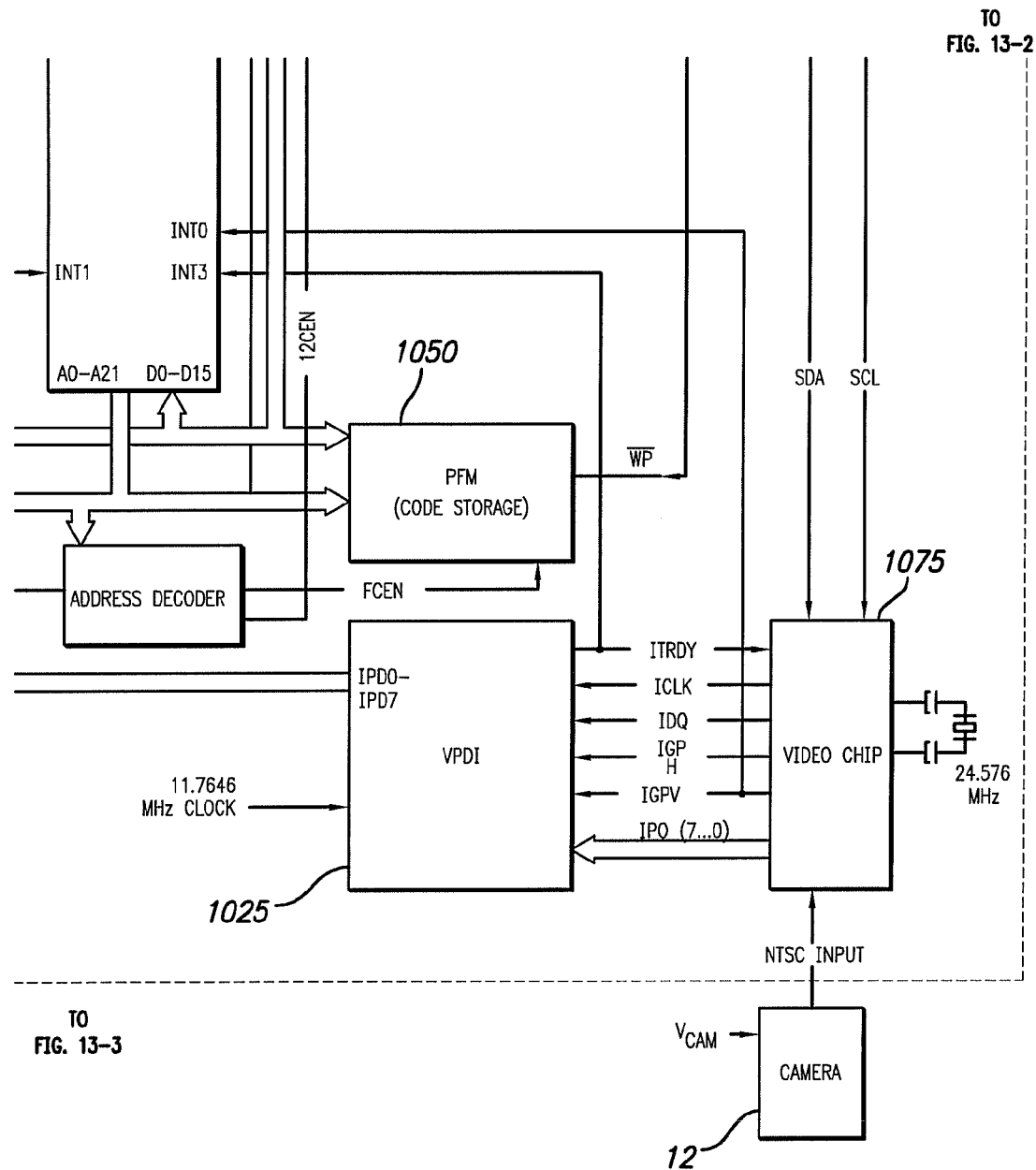

FIG. 6B shows an exploded view of the external coil arrangement 14 and mounting system 16. As also shown in FIGS. 6A and 7, the external coil arrangement 14 and mounting system 16 are connected by a flexible connector 1506. In particular, the flexible connector 1506 is attached to RF coil enclosure halves 1507 and 1508 on the coil side and to enclosure case halves 1509 and 1510 on the mounting system side. The external coil arrangement 14 comprises coil enclosure halves 1507 and 1508, enclosing printed circuit boards (PCB) 1511 and 1512 surrounding an RF transmitting coil 1513. The PCBs 1511 and 1512 may further include telemetry receiving coils. The mounting system 16 comprises case halves 1509 and 1510 enclosing an RF visor cable assembly 1514. Other mechanical components shown in FIG. 6B include: wires 1515 connecting PCBs 1511 and 1512; a mounting bracket 1516; and RF circuitry 1501 located between case halves 1509 and 1510. While video image processing is done in a VPU 20 (shown in FIGS. 11-12), the RF circuitry 1501 is incorporated into the mounting system 16 to reduce losses in the cable connecting the VPU 20 to the Glasses 5. PCBs 1511 and 1512 can be made of glass base epoxy and laminated with copper. An exemplary circuital diagram of RF circuitry 1501 is shown in FIGS. 13-1 to 13-4.

Figure 9:
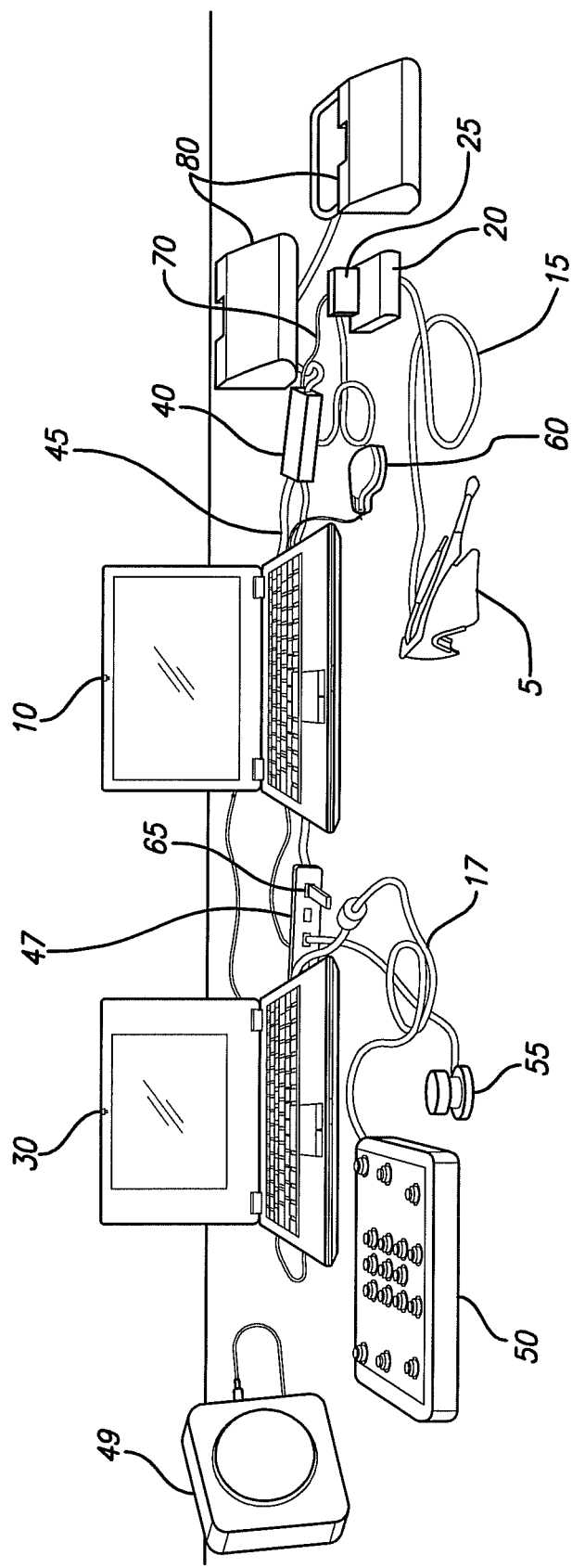
FIG. 9 shows components of a fitting system according to the present disclosure, the system also comprising the visor shown in FIGS. 6A-6B and 7.

Referring to FIG. 9, a Fitting System (FS) may be used to configure and optimize the visual prosthesis apparatus shown in FIG. 1. The Fitting System is fully described in the related application U.S. application Ser. No. 11/796,425, filed on Apr. 27, 2007, which is incorporated herein by reference in its entirety.

The Fitting System may comprise custom software with a graphical user interface running on a dedicated laptop computer 10. Within the Fitting System are modules for performing diagnostic checks of the implant, loading and executing video configuration files, viewing electrode voltage waveforms, and aiding in conducting psychophysical experiments. A video module can be used to download a video configuration file to the Video Processing Unit (VPU) 20 discussed above and store it in non-volatile memory to control various aspects of video configuration, e.g. the spatial relationship between the video input and the electrodes. The software can also load a previously used video configuration file from the VPU 20 for adjustment.

The Fitting System can be connected to the Psychophysical Test System (PTS), located for example on a dedicated laptop 30, in order to run psychophysical experiments. In psychophysics mode, the Fitting System enables individual electrode control, permitting clinicians to construct test stimuli with control over current amplitude, pulse-width, and frequency of the stimulation. In addition, the psychophysics module allows the clinician to record subject responses. The PTS may include a collection of standard psychophysics experiments developed using for example MATLAB (MathWorks) software and other tools to allow the clinicians to develop customized psychophysics experiment scripts.

Using the psychophysics module, important perceptual parameters such as perceptual threshold, maximum comfort level, and spatial location of percepts may be reliably measured. Based on these perceptual parameters, the fitting software enables custom configuration of the transformation between video image and spatio-temporal electrode stimulation parameters in an effort to optimize the effectiveness of the retinal prosthesis for each subject.

The Fitting System laptop 10 of FIG. 9 may be connected to the VPU 20 using an optically isolated serial connection adapter 40. Because it is optically isolated, the serial connection adapter 40 assures that no electric leakage current can flow from the Fitting System laptop 10 in the even of a fault condition.

As shown in FIG. 9, the following components may be used with the Fitting System according to the present disclosure. The Video Processing Unit (VPU) 20 for the subject being tested, a Charged Battery 25 for VPU 20, the Glasses 5, a Fitting System (FS) Laptop 10, a Psychophysical Test System (PTS) Laptop 30, a PTS CD (not shown), a Communication Adapter (CA) 40, a USB Drive (Security) (not shown), a USB Drive (Transfer) 47, a USB Drive (Video Settings) (not shown), a Patient Input Device (RF Tablet) 50, a further Patient Input Device (Jog Dial) 55, Glasses Cable 15, CA-VPU Cable 70, FS-CA Cable 45, FS-PTS Cable 46, Four (4) Port USB Hub 47, Mouse 60, Test Array system 80, Archival USB Drive 49, an Isolation Transformer (not shown), adapter cables (not shown), and an External Monitor (not shown).

With continued reference to FIG. 9, the external components of the Fitting System may be configured as follows. The battery 25 is connected with the VPU 20. The PTS Laptop 30 is connected to FS Laptop 10 using the FS-PTS Cable 46. The PTS Laptop 30 and FS Laptop 10 are plugged into the Isolation Transformer (not shown) using the Adapter Cables (not shown). The Isolation Transformer is plugged into the wall outlet. The four (4) Port USB Hub 47 is connected to the FS laptop 10 at the USB port. The mouse 60 and the two Patient Input Devices 50 and 55 are connected to four (4) Port USB Hubs 47. The FS laptop 10 is connected to the Communication Adapter (CA) 40 using the FS-CA Cable 45. The CA 40 is connected to the VPU 20 using the CA-VPU Cable 70. The Glasses 5 are connected to the VPU 20 using the Glasses Cable 15.

In one exemplary embodiment, the Fitting System shown in FIG. 9 may be used to configure system stimulation parameters and video processing strategies for each subject outfitted with the visual prosthesis apparatus of FIG. 1. The fitting application, operating system, laptops 10 and 30, isolation unit and VPU 20 may be tested and configuration controlled as a system. The software provides modules for electrode control, allowing an interactive construction of test stimuli with control over amplitude, pulse width, and frequency of the stimulation waveform of each electrode in the Retinal stimulation system 1. These parameters are checked to ensure that maximum charge per phase limits, charge balance, and power limitations are met before the test stimuli are presented to the subject. Additionally, these parameters may be checked a second time by the VPU 20's firmware. The Fitting System shown in FIG. 7 may also provide a psychophysics module for administering a series of previously determined test stimuli to record subject's responses. These responses may be indicated by a keypad 50 and or verbally. The psychophysics module may also be used to reliably measure perceptual parameters such as perceptual threshold, maximum comfort level, and spatial location of percepts. These perceptual parameters may be used to custom configure the transformation between the video image and spatio-tempral electrode stimulation parameters thereby optimizing the effectiveness of the visual prosthesis for each subject. The Fitting System is fully described in the related application U.S. application Ser. No. 11/796,425, filed on Apr. 27, 2007, which is incorporated herein by reference in its entirety.

Figure 10:
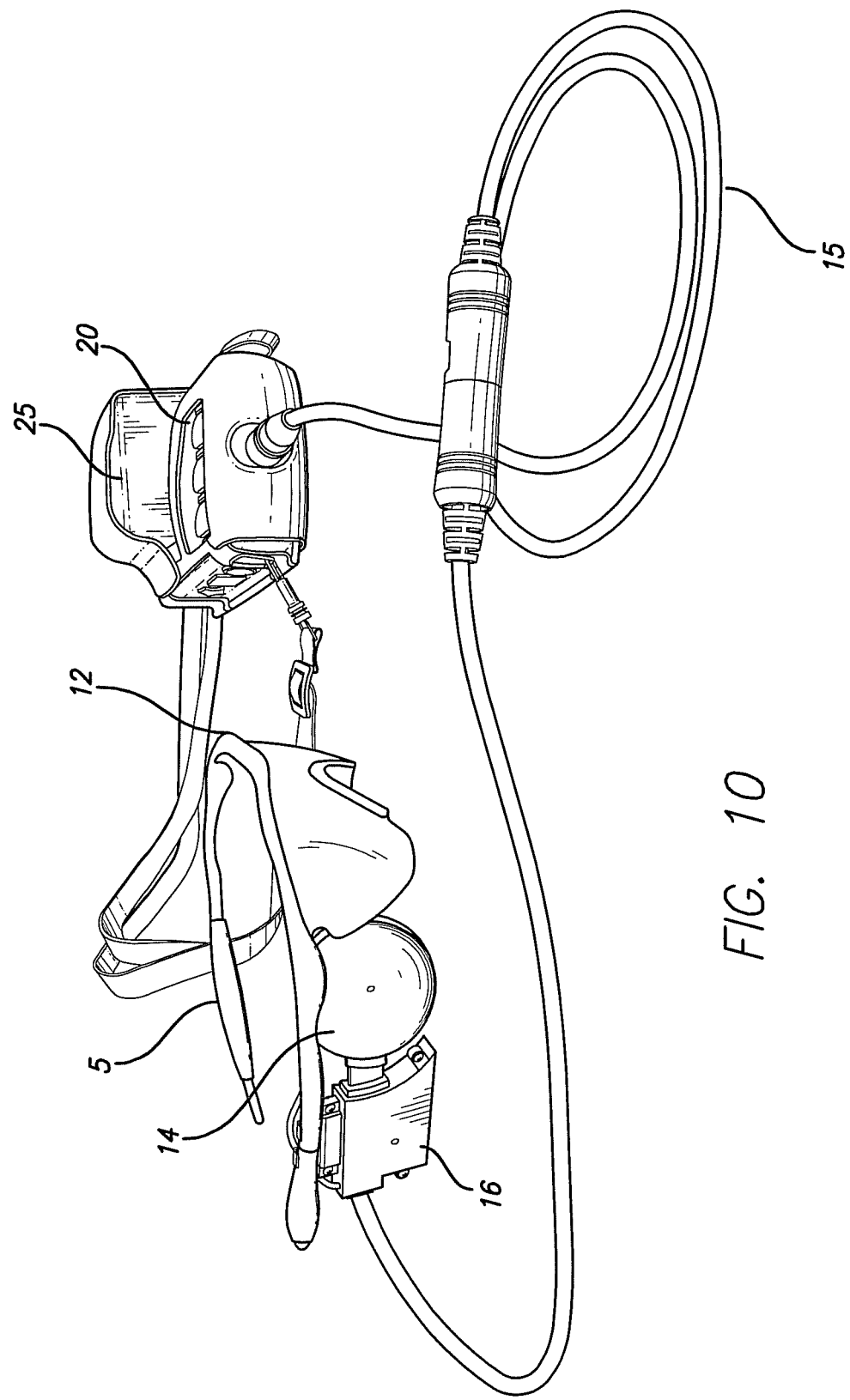
FIG. 10 shows the visual prosthesis apparatus in a stand-alone mode, i.e. comprising the visor connected to a video processing unit.
Figure 11A:
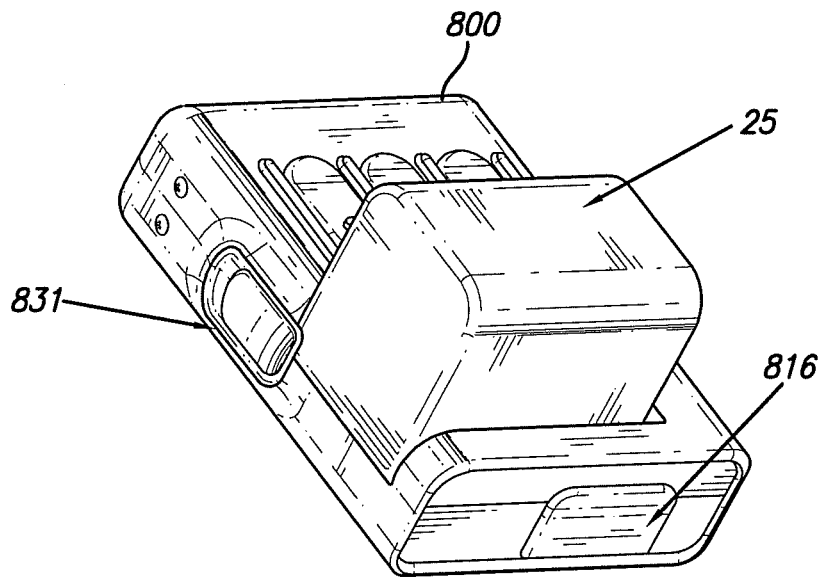

The visual prosthesis apparatus of FIG. 1 may operate in two modes: i) stand-alone mode and ii) communication mode Stand-Alone Mode Referring to FIGS. 1, 2 and 10, in the stand-alone mode, the video camera 12, on the glasses 5, captures a video image that is sent to the VPU 20. The VPU 20 processes the image from the camera 12 and transforms it into electrical stimulation patterns that are transmitted to the external coil 14. The external coil 14 sends the electrical stimulation patterns and power via radio-frequency (RF) telemetry to the implanted retinal stimulation system 1 (FIGS. 2 and 3). The internal coil 116 of the retinal stimulation system 1 receives the RF commands from the external coil 14 and transmits them to the electronics package 4 that in turn delivers stimulation to the retina via the electrode array 2. Additionally, the retinal stimulation system 1 may communicate safety and operational status back to the VPU 20 by transmitting RF telemetry from the internal coil 116 to the external coil 14. The visual prosthesis apparatus of FIG. 1 may be configured to electrically activate the retinal stimulation system 1 only when it is powered by the VPU 20 through the external coil 14. The stand-alone mode may be used for clinical testing and/or at-home use by the subject.

Communication Mode

The communication mode may be used for diagnostic testing, psychophysical testing, patient fitting and downloading of stimulation settings to the VPU 20 before transmitting data from the VPU 20 to the retinal stimulation system 1 as is done for example in the stand-alone mode described above. Referring to FIG. 9, in the communication mode, the VPU 20 is connected to the Fitting System laptop 10 using cables 70, 45 and the optically isolated serial connection adapter 40. In this mode, laptop 10 generated stimuli may be presented to the subject and programming parameters may be adjusted and downloaded to the VPU 20. The Psychophysical Test System (PTS) laptop 30 connected to the Fitting System laptop 10 may also be utilized to perform more sophisticated testing and analysis as fully described in the related application U.S. application Ser. No. 11/796,425, filed on Apr. 27, 2007, which is incorporated herein by reference in its entirety.

In one embodiment, the functionality of the retinal stimulation system 1 can also be tested pre-operatively and intra-operatively (i.e. before operation and during operation) by using an external coil 14, without the glasses 5, placed in close proximity to the retinal stimulation system 1. The coil 14 may communicate the status of the retinal stimulation system 1 to the VPU 20 that is connected to the Fitting System laptop 10 as shown in FIG. 9.

As discussed above, the VPU 20 processes the image from the camera 12 and transforms the image into electrical stimulation patterns for the retinal stimulation system 1. Filters such as edge detection filters may be applied to the electrical stimulation patterns for example by the VPU 20 to generate, for example, a stimulation pattern based on filtered video data that the VPU 20 turns into stimulation data for the retinal stimulation system 1. The images may then be reduced in resolution using a downscaling filter. In one exemplary embodiment, the resolution of the image may be reduced to match the number of electrodes in the electrode array 2 of the retinal stimulation system 1. That is, if the electrode array has, for example, sixty electrodes, the image may be reduced to a sixty channel resolution. After the reduction in resolution, the image is mapped to stimulation intensity using for example a look-up table that has been derived from testing of individual subjects. Then, the VPU 20 transmits the stimulation parameters via forward telemetry to the retinal stimulation system 1 in frames that may employ a cyclic redundancy check (CRC) error detection scheme.

In one exemplary embodiment, the VPU 20 may be configured to allow the subject/patient i) to turn the visual prosthesis apparatus on and off, ii) to manually adjust settings, and iii) to provide power and data to the retinal stimulation system 1. Referring to FIGS. 11 and 12, the VPU 20 may comprise a case 800, power button 805 for turning the VPU 20 on and off, setting button 810, zoom buttons 820 for controlling the camera 12, connector port 815 for connecting to the Glasses 5, a connector port 816 for connecting to the laptop 10 through the connection adapter 40, indicator lights 825 to give visual indication of operating status of the system, the rechargeable battery 25 for powering the VPU 20, battery latch 831 for locking the battery 25 in the case 800, digital circuit boards (not shown), and a speaker (not shown) to provide audible alerts to indicate various operational conditions of the system. Because the VPU 20 is used and operated by a person with minimal or no vision, the buttons on the VPU 20 may be differently shaped and/or have special markings as shown in FIG. 12 to help the user identify the functionality of the button without having to look at it. As shown in FIG. 12, the power button 805 may be a circular shape while the settings button 820 may be square shape and the zoom buttons 820 may have special raised markings 830 to also identify each buttons functionality. One skilled in the art would appreciate that other shapes and markings can be used to identify the buttons without departing from the spirit and scope of the invention. For example, the markings can be recessed instead of raised.

In one embodiment, the indicator lights 825 may indicate that the VPU 20 is going through system start-up diagnostic testing when the one or more indicator lights 825 are blinking fast (more then once per second) and are green in color. The indicator lights 825 may indicate that the VPU 20 is operating normally when the one or more indicator lights 825 are blinking once per second and are green in color. The indicator lights 825 may indicate that the retinal stimulation system 1 has a problem that was detected by the VPU 20 at start-up diagnostic when the one or more indicator lights 825 are blinking for example once per five second and are green in color. The indicator lights 825 may indicate that the video signal from camera 12 is not being received by the VPU 20 when the one or more indicator lights 825 are always on and are amber color. The indicator lights 825 may indicate that there is a loss of communication between the retinal stimulation system 1 and the external coil 14 due to the movement or removal of Glasses 5 while the system is operational or if the VPU 20 detects a problem with the retinal stimulation system 1 and shuts off power to the retinal stimulation system 1 when the one or more indicator lights 825 are always on and are orange color. One skilled in the art would appreciate that other colors and blinking patterns can be used to give visual indication of operating status of the system without departing from the spirit and scope of the invention.

In one embodiment, a single short beep from the speaker (not shown) may be used to indicate that one of the buttons 825, 805 or 810 have been pressed. A single beep followed by two more beeps from the speaker (not shown) may be used to indicate that VPU 20 is turned off. Two beeps from the speaker (not shown) may be used to indicate that VPU 20 is starting up. Three beeps from the speaker (not shown) may be used to indicate that an error has occurred and the VPU 20 is about to shut down automatically. As would be clear to one skilled in the art different periodic beeping may also be used to indicate a low battery voltage warning, that there is a problem with the video signal, and/or there is a loss of communication between the retinal stimulation system 1 and the external coil 14. One skilled in the art would appreciate that other sounds can be used to give audio indication of operating status of the system without departing from the spirit and scope of the invention. For example, the beeps may be replaced by an actual prerecorded voice indicating operating status of the system.

In one exemplary embodiment, the VPU 20 is in constant communication with the retinal stimulation system 1 through forward and backward telemetry. In this document, the forward telemetry refers to transmission from VPU 20 to the retinal stimulation system 1 and the backward telemetry refers to transmissions from the Retinal stimulation system 1 to the VPU 20. During the initial setup, the VPU 20 may transmit null frames (containing no stimulation information) until the VPU 20 synchronizes with the Retinal stimulation system 1 via the back telemetry. In one embodiment, an audio alarm may be used to indicate whenever the synchronization has been lost.

In order to supply power and data to the Retinal stimulation system 1, the VPU 20 may drive the external coil 14 with a 3 MHz signal. To protect the subject, the retinal stimulation system 1 may comprise a failure detection circuit to detect direct current leakage and to notify the VPU 20 through back telemetry so that the visual prosthesis apparatus can be shut down.

One exemplary embodiment of the VPU 20 is shown in FIGS. 13-1, 13-2, 13-3 and 13-4. As shown in FIGS. 13-1, 13-2, 13-3 and 13-4, the VPU 20 may comprise: a Power Supply, a Distribution and Monitoring Circuit (PSDM) 1005, a Reset Circuit 1010, a System Main Clock (SMC) source (not shown), a Video Preprocessor Clock (VPC) source (not shown), a Digital Signal Processor (DSP) 1020, Video Preprocessor Data Interface 1025, a Video Preprocessor 1075, an I²C Protocol Controller 1030, a Complex Programmable Logic device (CPLD) (not shown), a Forward Telemetry Controller (FTC) 1035, a Back Telemetry Controller (BTC) 1040, Input/Output Ports 1045, Memory Devices like a Parallel Flash Memory (PFM) 1050 and a Serial Flash Memory (SFM) 1055, a Real Time Clock 1060, an RF Voltage and Current Monitoring Circuit (VIMC) 1071, a speaker and/or a buzzer (not shown), an RF receiver 1065, and an RF transmitter 1070.

In one exemplary embodiment, the VPU 20 is a battery 25 powered micro-controller-based video processing and radio-frequency (RF) transceiver system. The VPU 20 may be comprised of a digital circuit for processing video from camera 12 (see FIG. 10) and an RF circuit 1501, shown in FIG. 13-1, to facilitate 2-way communication with the retinal stimulation system 1. In one exemplary embodiment, the RF circuit 1501 may be mounted in the enclosure 1510 on the visor/Classes 5 in close proximity to the retinal stimulation system 1 while the digital circuit of the VPU 20 can be remotely located in a case 800 shown in FIGS. 11A-E and described below. The mechanical design, shown in FIG. 10, may include a multiple-conductor cable 15 linking the VPU 20 and RF circuits 1501 disposed in the mounting system 16 as shown in FIGS. 6A and 6B. In another exemplary embodiment, the RF circuits 1501 may further comprise all the elements shown in FIGS. 13-1 to 13-4 that are disposed on the visor/Classes 5 in the mounting system 16.

In an exemplary embodiment, the digital circuit of the VPU 20 accepts an incoming analog video stream from a small camera 12 mounted on the Glasses 5, which may have the appearance of a pair of sunglasses. The analog video stream from the camera 12 is converted to a digital video stream by the Video Preprocessor 1075 of the VPU 20. The digital video stream is then stored into memory as individual video frames typically by means of a direct memory access (DMA) circuit specifically designed to accept digital video, called the video preprocessor data interface (VDPI) 1025 shown in FIG. 13-4. The VDPI 1025 of the VPU 20 processes the video frames stored in its memory into packets of stimulation information. The stimulation information is passed to the RF circuit 1501 via a serial port and an encoder circuit within the forward telemetry controller (FTC) 1035. The RF transmitter circuit 1070 receives the stimulation information and transmits it to the retinal stimulation system 1 via a magnetically coupled coil 14. The RF signal within the coil 14 has sufficient strength to power the retinal stimulation system 1. The RF circuit 1501 is also capable of receiving back-telemetry information (containing status and safety related data) from the retinal stimulation system 1 via a coil connected to a receiver circuit 1065. The received data is passed to a decoder circuit within the back telemetry controller (BTC) 1040 and then to a serial port, which allows the VDPI 1025 to examine the received data. The power supply, distribution and monitoring circuit (PSDM) 1005 generates all of the appropriate voltages and contains a programmable power supply for the RF circuit 1501 to allow adjustment of the power level to the retinal stimulation system 1.

The Power Supply, Distribution and Monitoring Circuit (PSDM) 1005 may regulate a variable battery voltage to several stable voltages that apply to components of the VPU 20. The Power Supply, Distribution and Monitoring Circuit (PSDM) 1005 may also provide low battery monitoring and depleted battery system cutoff. The PSDM 1005 may be configured to provide Digital Circuit Voltage (VDD) 3.3±0.1V@300 mA; 300 mV ripple. The PSDM 1005 may be configured to provide DSP Core Voltage (CVDD1) 1.6±0.1V@100 mA; 200 mV ripple. The PSDM 1005 may be configured to provide CPLD Core Voltage (CVDD2) 1.8±0.1V@50 mA; 200 mV ripple. The PSDM 1005 may be configured to provide Abalog Voltage (VA) 3.3±0.1V@100 mA; 300 mV ripple. The PSDM 1005 may be configured to provide Camera Voltage ($V_{CAM}$) 5.0±0.25V@100 mA; 300 mV ripple. The PSDM 1005 may be configured to provide RF Voltage 185 mV/step ($V_{rf}$) 4.75V~10.5V±0.3V@75 mA; 300 mV ripple. The PSDM 1005 may be configured to provide Fixed Voltage (FV) 3.3±0.1V@25 mA; 100 mV ripple. In one exemplary embodiment, the RF voltage ($V_{rf}$) may be fused on the RF circuit as a failsafe mechanism to protect against excessive current in case of a malfunction.

In one exemplary embodiment, the VPU 20 stops providing power/data to the retinal stimulation system 1 and/or turns itself off when the PSDM 1005 detects that the battery 25's (FIG. 10) voltage decreases to a predetermined voltage. The predetermined voltage may, for example, be 6.75±0.4 volts. In one exemplary embodiment, the battery 25's voltage may be fused at the battery connector (not shown) as a fail-safe mechanism to protect against excessive current in case of malfunction. In another exemplary embodiment, the battery 25's drain current may be less than 1 mA when VPU 20 is turned off.

The Reset Circuit 1010 may have reset inputs 1011 that are able to invoke a system level reset. For example, the reset inputs 1011 may be from a manual push-button reset, a watchdog timer expiration, and/or firmware based shutdown. The manual push-button reset may be, for example, low active when pulse width is >1 ms. The watchdog timer reset may be activated when the watchdog timer is not reset within a predetermined expiration time, wherein the watchdog timer should be reset every 1.0 seconds or less if the expiration time ranges, for example, from 1.0 to 2.25 seconds. The firmware-based shutdown may be activated when the firmware evokes, for example, a falling edge signal.

The System Main Clock (SMC) source is a clock source for DSP 1020 and CPLD. The SMC may be, for example, 11.7846 MHz+/−50 ppm. The Video Preprocessor Clock (VPC) source is a clock source for the Video Processor and the VPC may be, for example, 24.576 MHz+/−50 ppm.

The DSP 1020 may act as the central processing unit of the VPU 20. In one exemplary embodiment, the DSP 1020 is a Texas Instruments (TI) TMS 320VC5416PGE160. "TMS320VC5416PGE160 Fixed-Point Digital Signal Processor Data Manual" from TI is incorporated herein by reference. The DSP 1020 may communicate with the rest of the components of the VPU 20 through parallel and serial interfaces. The parallel interface of the DSP 1020 may create a Program Space (PS), a Data Space (DS) and Input/Output Space (IOS), wherein the executable code is allocated to PS, the data is allocated to the DS and I/O devices are allocated to IOS. The serial interface DSP 1020 may contain three Multi-channel Buffered Serial Ports (McBSPs), wherein McBSP0 is configured in continuous clock mode for PC communication, McBSP1 is configured in non-continuous clock Serial Port Interface (SPI) mode for interface to the serial flash memory, and McBSP2 is configured in continuous clock mode for the RF transceiver.

The Video Processor 1075 may convert the NTSC signal from the camera 12 into a down-scaled resolution digital image format. In one exemplary embodiment, the Video Processor 1075 is a Philips Semiconductor SAA7114H. The Video Processor 1075 may comprise a video decoder (not shown) for converting the NTSC signal into high-resolution digitized image and a video scaler (not shown) for scaling down the high-resolution digitized image from the video decoder to an intermediate digitized image resolution. The video decoder of the Video Processor 1075 may be composed of an Analog Input Processing, Chrominance and Luminance Processing and Brightness Contrast and Saturation (BSC) Control circuits. The video scaler may be composed of Acquisition control, Pre-scaler, BSC-control, Line Buffer and Output Interface.

The I$^2$C Protocol Controller 1030 may serve as a link between the DSP 1020 and the I$^2$C bus. In one exemplary embodiment, the I$^2$C Protocol Controller 1030 is a Philips Semiconductor PCA9564. The I$^2$C Protocol Controller 1030 may be able to convert the parallel bus interface of the DSP 1020 to the I$^2$C protocol bus or vise versa. The I$^2$C Protocol Controller 1030 may also be connected to the Video Processor 1075 having, for example, a Read Address 43H and a Write Adress 42H and the I$^2$C Protocol Controller 1030 may be connected to the Real Time Clock 1060 wherein the clock control registers use, for example, read address 0DFH and write address 0DEH and wherein the EEPROM array uses, for example, read address 0AFH and a write address 0AEH.

The Complex Programmable Logic Device (CPLD) (not shown) furnishes the physical device for the multiple digital logic circuits. Memory space allocation: the executable code may be mapped to parallel flash memory device that is located at off-DSP space (PS 00000H~7FFFFH). The peripheral devices may be mapped to IOS as follows: Status/Timeput Port of the I$^2$C communication device may be mapped to 2000H; Data Port of the I$^2$C communication device may be mapped to 2001H; Own Address Port of the I$^2$C communication device may be mapped to 2002H; and Control Port of the I$^2$C communication device may be mapped to 2003H; Input port1 of the CPLD device may be mapped to 4000H; Inputport2 of the CPLD device may be mapped to 4001H; VideoDataInput of the CPLD device may be mapped to 4002H; CPLDVersion of the CPLD device may be mapped to 4003H; VideoLineCount of the CPLD device may be mapped to 4004H; OutputPort1 of the CPLD device may be mapped to 4008H; OutputPort2 of the CPLD device may be mapped to 400AH; OutputPort3 of the CPLD device may be mapped to 400BH; ADconvst of the CPLD device may be mapped to 6000H; ADCeN[1 . . . 0] of the CPLD device may be mapped to 8000~8003H; and KeypadInput of the CPLD device may be mapped to A000H.

The VPDI 1025 may contain a tri-state machine to shift video data from Video Preprocessor 1075 to the DSP 1020. Signal ITRDY of the VPDI 1025 may be connected to Video Chip 1075 and DSP 1020 and may be used to indicate the status of shifting and to facilitate rapid response in transferring video data. In one exemplary embodiment, a high level signal ITRDY indicates to VPU 20 that VPDI 1025 is empty and ready to accept next data, and a low level signal ITRDY indicates to the VPU 20 that VPDI 1025 is full and the Video Preprocessor 1075 should hold in the Video Preprocessor 1075's internal FIFO (not shown). In one exemplary embodiment, the VPDI 1025 may have a coupling signal FreeVideo that enables or disables the VPDI 1025's functionality.

The Forward Telemetry Controller (FTC) 1035 of FIG. 13-1 may pack 1024 bits of forward telemetry data into a forward telemetry frame. The FTC 1035 retrieves the forward telemetry data from the DSP 1020's McBSP2 port and converts the data from logic level to biphase marked data. The FTC 1035 may generate BCLKX2 and BFSX2 signals to the DSP 1020's MCBSP2 port. In one exemplary embodiment, the BCLKX2 signal may be a serial data clock for forward telemetry data and the BFSX2 signal may be an FX frame synchronization signal that may indicate that a first bit of each 16-bit word is generated by the serial part (MCBSP2). To improve reliability of data transmission, the FTC 1035 may also convert a logic '1' to a double bit frequency signal and a logic '0' to as single bit frequency signal. In one exemplary embodiment, logic '1' may be converted to two (2) logic level transitions between the data clock signal (double frequency) and logic '0' may be converted to one (1) transition (single frequency). The word data in the DSP 1020 may be synchronized with the FTC 1035's counter through Frame Counter Starter (FCS) (not shown). The FTC 1035 may also have logic circuit for decoding a specific pattern of 1's and zeros (for example, 0100 1110 1010 0011) that indicate the beginning of a forward telemetry frame. As soon as the FTC 1035 receives a predefined word, FTC 1035's line counter begins to count down and is ready to accept the forward telemetry data. In one exemplary embodiment, the FTC 1035 may have an FTC reset functionality that causes the FTC 1035 to reset upon VPU 20's start up.

The Back Telemetry Controller (BTC) 1040 retrieves the biphase marked data from the RF receiver 1065, decodes it, and generates the BFSR and bit clock (BCLKR) for the DSP

1020's McBSP2 interface. The BCLKR may be generated based on a decoded biphase marked data. In one exemplary embodiment, the biphase marked data may be received from the retinal stimulation system 1 and may be converted similarly to FTC 1035. The Back Telemetry Controller (BTC) 1040 may also have a header detector (not shown) that monitors decoded data for predefined word header, for example, "1111111111111110." Upon detection of the predefined word header, a back telemetry word frame BFSR signal may be pulsed. If the BFSR signal occurs greater than 32 bits apart, an error bit may be set. The BFSR and BCLKR signal DSP 1020's McBSP2 port to receive data on the BDR2 input. The date rate on the BDR2 input may be 3.84±0.2 Kbps. Error bits may be set if the rate of modulation state change too fast or too slow.

The Input/Output Ports 1045 provide expanded 10 functions to access the CPLD on-chip and off-chip devices. An InputPort1 (see Table 1) of the Input/Output Ports 1045 may have an address IOS 4000h and may provide off chip input access. An InputPort2 (see Table 2) of the Input/Output Ports 1045 may have an address IOS 4001h and may provide off chip input access. A VideoDataInput (see Table 3) of the Input/Output Ports 1045 may have an address IOS 4002h and may provide on chip input access. A CPLD_Version (see Table 4) of the Input/Output Ports 1045 may have an address IOS 4003h and may provide on chip input access. A VideoLineCount (see Table 5) of the Input/Output Ports 1045 may have an address IOS 4004h and may provide on chip input access. An OutputPort1 (see Table 6) of the Input/Output Ports 1045 may have an address IOS 4008h and may provide on chip and off chip output access. The initial value of the OutputPort1 may be 0000h at system reset. An OutputPort2 (see Table 7) of the Input/Output Ports 1045 may have an address IOS 400Ah and may provide on chip output access. The initial value OutputPort2 may be 0001h at system reset. An ADconvst (see Table 8) of the Input/Output Ports 1045 may have an address IOS 6000h and may provide off chip output access. An ADCeN (see Table 9) of the Input/Output Ports 1045 may have an address IOS 8000H~8003H and may provide off-chip input access. An OutputPort3 (see Table 10) of the Input/Output Ports 1045 may have an address IOS 400Bh and may provide off-chip output access. The initial value of the OutputPort3 may be 0000h at system reset. A KeypadInput (see Table 11) of the Input/Output Ports 1045 may have an address IOS A000h and may provide off chip input access.

TABLE 1

InputPort1 Definition

Bit Function

0 Reserved
1 Frame Sync Slow Detect 1. 1 = Slow Frame Sync Detected (greater than 32 bits apart), 0 = Slow Frame Sync not detected. Write a zero to this bit or system reset to clear it.
2 Slow Modulation rate detect (greater than 348 usec per state). 1 = Slow modulation rate detected, 0 = Slow modulation rate not detected. Write a zero to bit 2 or bit 3 at this address or system reset to clear this bit.
3 Fast Modulation rate detect (between 43.5 and 87 usec per state). 1 = Fast modulation rate detected, 0 = Fast modulation rate not detected. Write a zero to bit 2 or bit 3 at this address or system reset to clear this bit.
4 Watchdog status. 1 = Watchdog timer has not expired. 0 = Watchdog timer has expired. This bit is set to the 1 state when the watchdog timer is subsequently reset.
5 0
6 0
7 0

TABLE 2

InputPort2 Definition

Bit Function

0 CA detection. 1 = CA connection is detected, 0 = CA connection is not detected.
1 Low Battery Detection. 1 = Normal battery voltage, 0 = Low Battery is detected.
2 Reserved
3 Connect Verify. 1 = Camera/RF connector not connected, 0 = Camera/RF connector connected.
4 Utility Key 8. 0 = Key not depressed, 1 = Key depressed
5 Program/Run Switch Position. 1 = Switch in Program position, 0 = Switch in Run position.
6 Reserved
7 Reserved

TABLE 3

VideoDataInput Definition

| Bit | Function |
| --- | --- |
| 0~7 | Video data input port |

TABLE 4

CPLD_Version Definition

| Bit | Function |
| --- | --- |
| 0~7 | CPLD Version number, 8 bits |

TABLE 5

VideoLine Count Definition

| Bit | Function |
| --- | --- |
| 0~7 | NTSC line counter. An 8-bit counter to count the NTSC line |

TABLE 6

OutputPort1 Definition

| Bit | Function |
|---|---|
| 0~4 | RF power control. 00000 = 4.75 +/− 0.3 V, 11111 = 10.5 +/− 0.3 V |
| 5 | System Running LED Indicator. 1 = turn the System Running LED on, 0 = turn the System Running LED off. |
| 6 | RF Link LED Indicator. 1 = turn the RF Link LED on, 0 = turn the RF Link off. |
| 7 | Camera Disconnect LED Indicator. 1 = turn the LED on, 0 = turn the LED off |

TABLE 7

OutputPort2 Definition

| Bit | Function |
|---|---|
| 0 | freeVideo, the VPDI coupling signal. 1 = VPDI is disabled, 0 = VPDI is enabled |
| 1~2 | Reserved |
| 3 | Shutdown, normally 0, set to 1 for at least 1 msec and then back to 0 to force a system shutdown |
| 4 | Reserved |
| 5~6 | Forward Telemetry BFSX signal start signal, 11 = command the BFSX to generate the word frame signal, 00 = no BFSX word frame signal. May be changed from 00 to 11 within one system bus cycle |
| 7 | Carrier enable. 1 = enable the carrier clock to the RF circuit and the BCLK to McBSP2, 0 = disable carrier clock and BCLK which are forced to output a low signal state |

TABLE 8

ADconvst Definition

| Bit | Function |
|---|---|
| 0~7 | AD converter sampling start trigger signal. Access of this port does not cause any data transfer between DSP, CPLD and AD converter. A low-active 50-300 nsec pulse from a dummy read access is used to trigger the AD converter to sample the signal |

TABLE 9

ADCeN Definition

| Address | Bit | Function |
|---|---|---|
| 8000H | 0~7 | Read present A/D data and select Channel 1 (the Vrf current) for the subsequent A/D sample. Each count for channel 1 data may represent 2.35 mA; the range may be 0 to 602 mA |
| 8001H | 0~7 | Read present A/D data and select Channel 2 (the Vrf voltage) for the subsequent A/D sample. Each count for channel 2 data may represent 43.32 mV; the range may be 0 to 11.05 V |
| 8002H | 0~7 | Reserved |
| 8003H | 0~7 | Reserved |

TABLE 10

OutputPort3 Definition

| Bit | Function |
|---|---|
| 0 | A/D converter power up/down, 0 = power down, 1 = power up |
| 1 | Vrf control, 0 = Vrf powered off, 1 = Vrf powered on |
| 2 | Watchdog counter reset signal. The watchdog counter is reset when the state of this bit is changed |
| 3~5 | Reserved |
| 6 | Buzzer control, 1 = turn the buzzer on, 0 = turn the buzzer off |
| 7 | Reserved |

TABLE 11

KeypadInput Definition

| Bit | Function |
|---|---|
| 0 | Utility Key 0. 1 = Key not depressed, 0 = Key depressed |
| 1 | Utility Key 1. 1 = Key not depressed, 0 = Key depressed |
| 2 | Utility Key 2. 1 = Key not depressed, 0 = Key depressed |
| 3 | Utility Key 3. 1 = Key not depressed, 0 = Key depressed |
| 4 | Utility Key 4. 1 = Key not depressed, 0 = Key depressed |
| 5 | Utility Key 5. 1 = Key not depressed, 0 = Key depressed |
| 6 | Utility Key 6. 1 = Key not depressed, 0 = Key depressed |
| 7 | Utility Key 7. 1 = Key not depressed, 0 = Key depressed |

In one exemplary embodiment, the buzzer (Table 10) may be from Soberton Inc. part number ST-03BL audio buzzer that operates at 2.3 KHz. The buzzer may provide a sound pressure level of 68-82 dB at 5 cm distance without an enclosure.

The VPU 20 shown in FIGS. 11-12 and 13-1-13-4 may have attachable/detachable ports 815-816 shown in FIGS. 11-12 to connect several peripheral units. The connectors are classified as functional connectors, e.g. port 815 and development connectors. The functional connectors link the functional peripheral devices, for example, Glasses 5 of FIG. 6 to the VPU 20 to furnish a production level function for the system. The development connectors may be used when the system is under development phase.

Figure 11B:
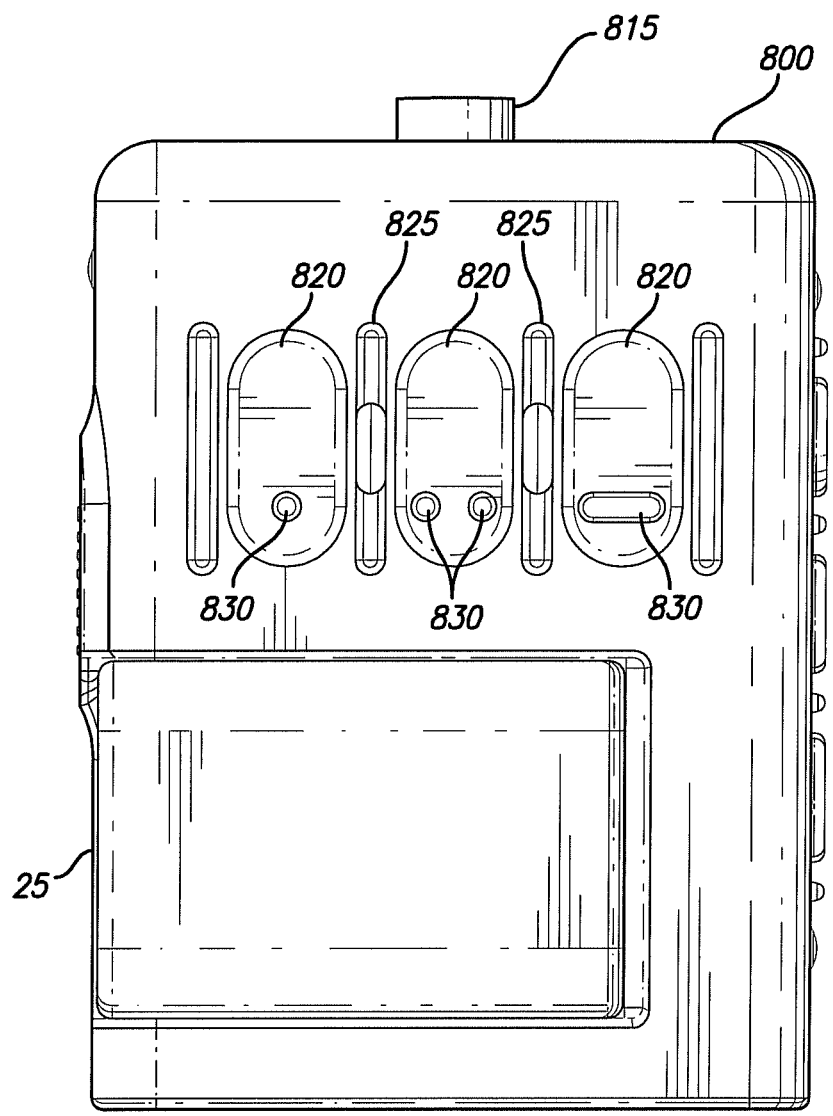
Figure 11D:
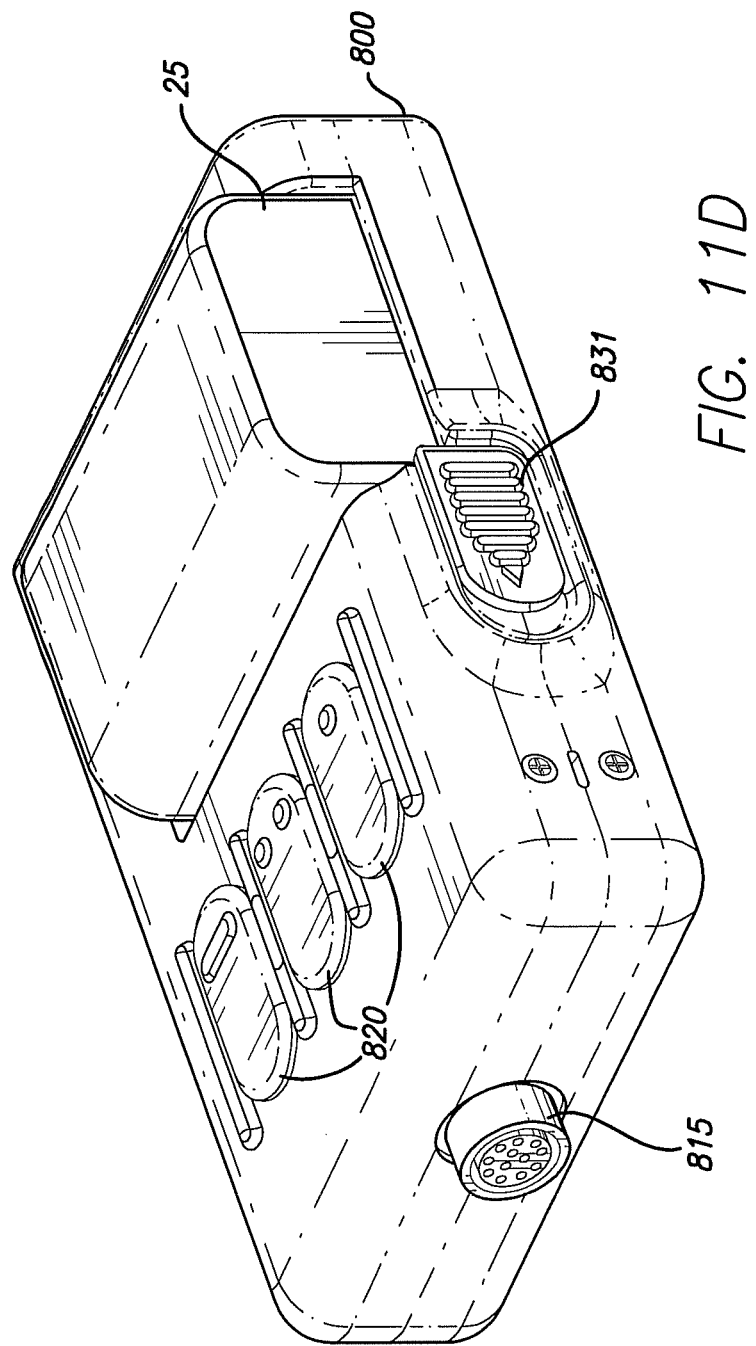
Figure 11E:
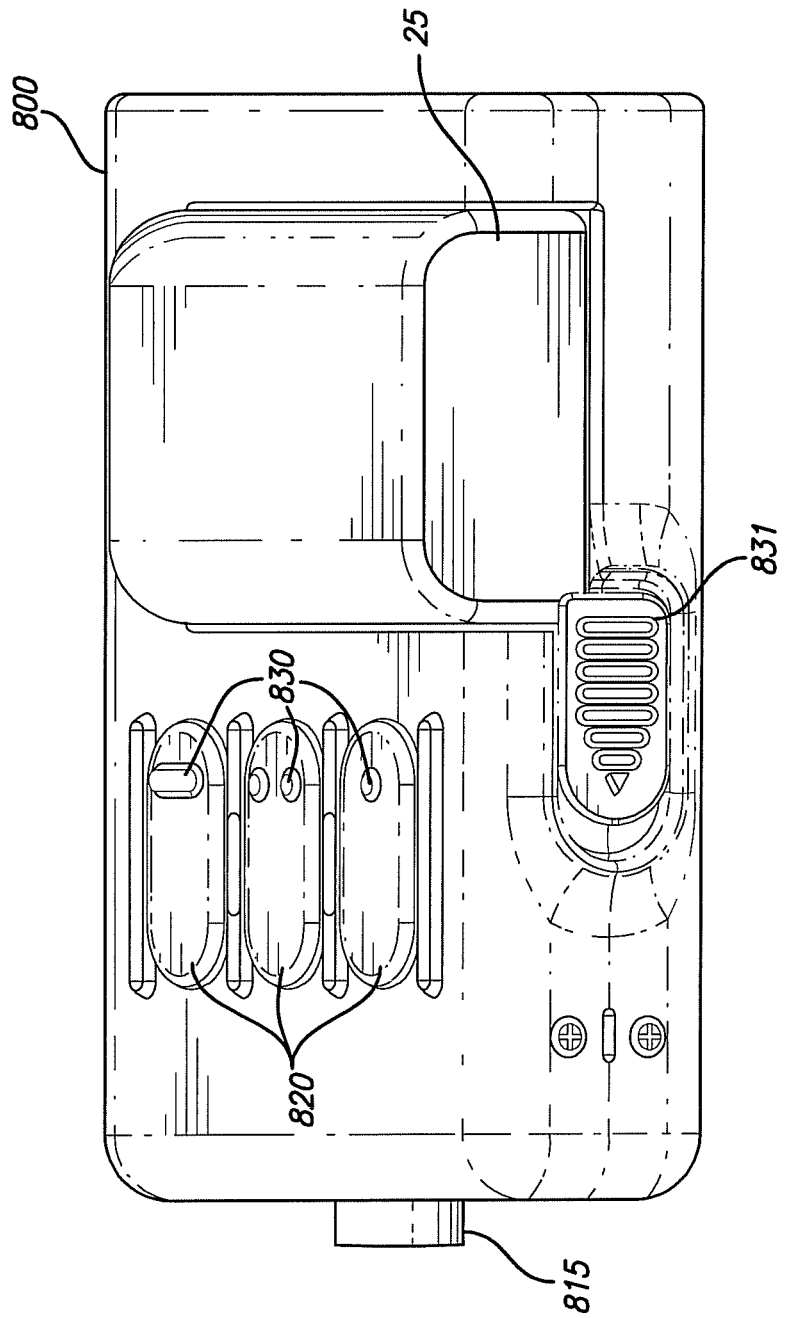
Figure 11F:
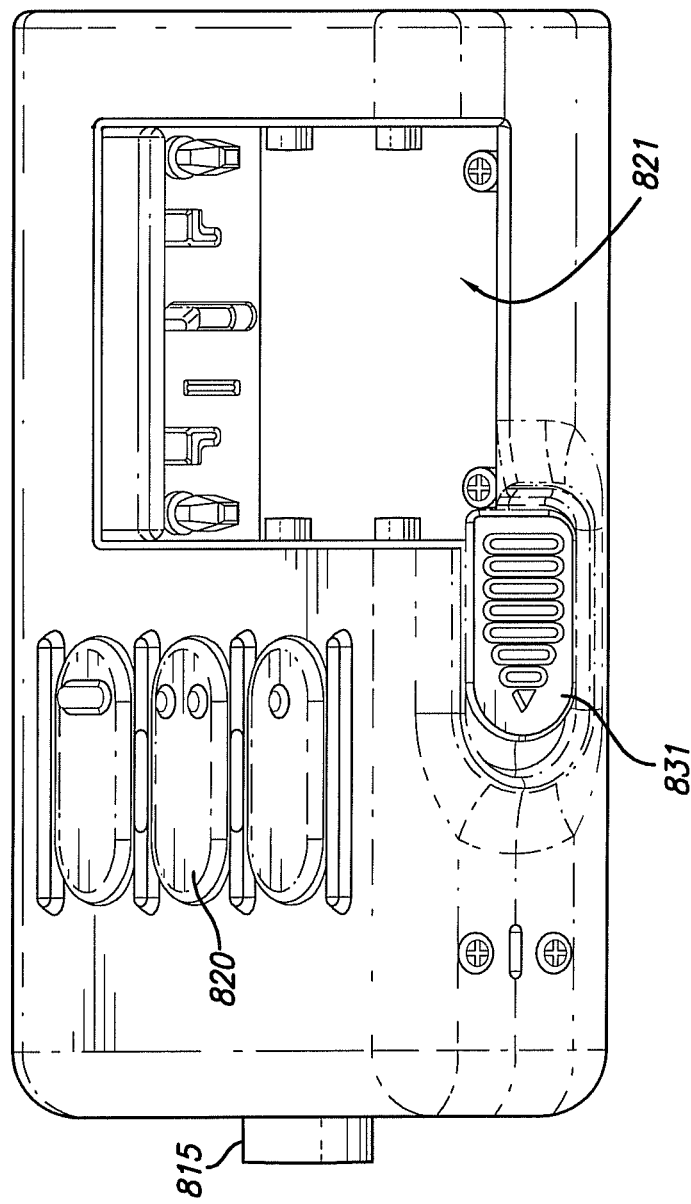
Figure 11G:
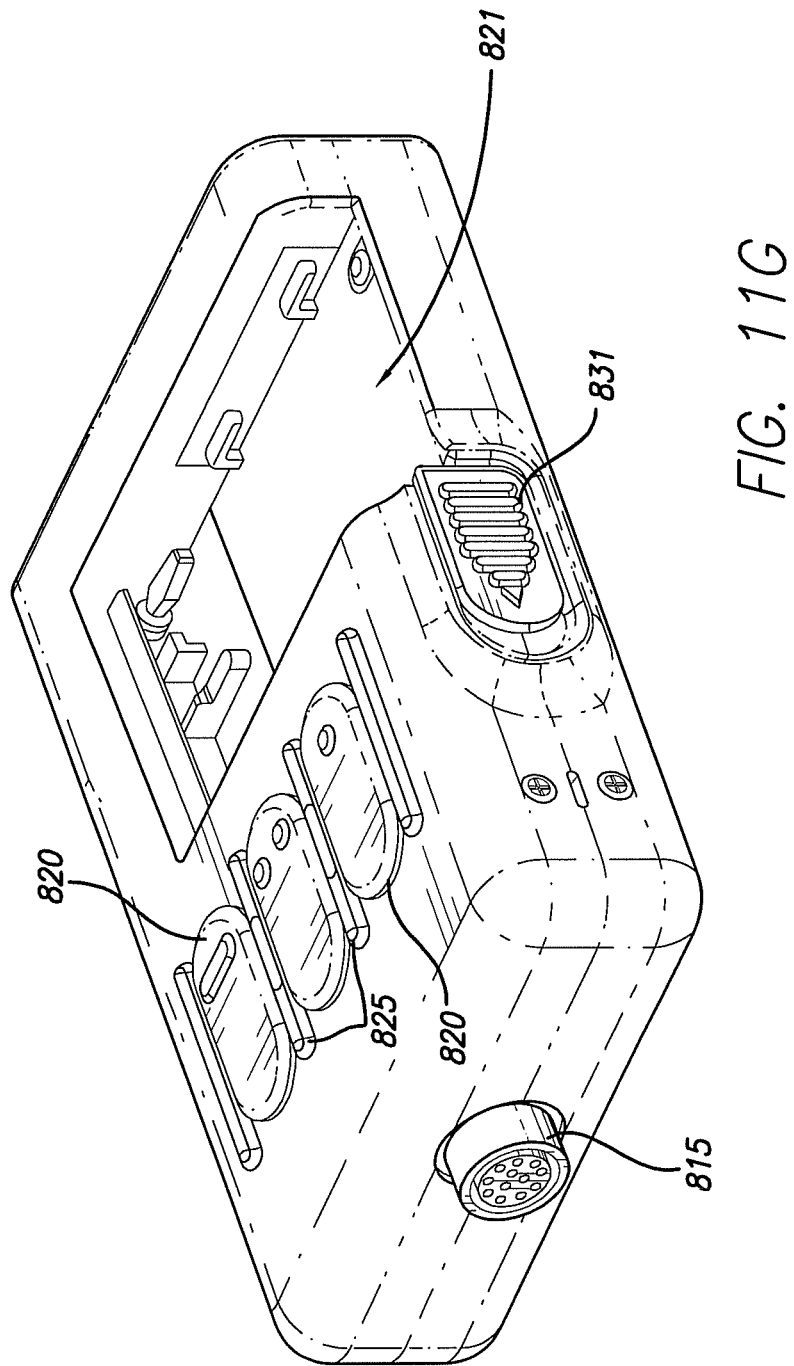

The Power Connector 821 shown in FIGS. 11F-11G (connector under the battery 25 in FIG. 11A) is a functional connector that connects the battery 25 to the VPU 20.

Port 815 is a functional Camera/RF Connector. Port 815 may contain 12 pins (identified in Table 12 below) to provide connection for the camera 12 and external coil 14 on the Glasses 5. The port 815 may be protected such that port 815 will withstand an indefinite short to the camera 12's power. The power connector and the port 815 may be mechanically keyed to prevent improper installation.

TABLE 12

Camera/RF Connector Pin Definition

| Pin | Name | Type | Function |
|---|---|---|---|
| 1 | Vrf | Power | RF voltage source |
| 2 | RF_GND | Power | Ground return for RF voltage source |
| 3 | BK_TEL | Input | Back Telemetry Data from RF Board |
| 4 | Carrier | Output | Carrier signal to RF Board |
| 5 | Data | Output | Forward Telemetry data to RF Board |
| 6 | Connect Verify | Input | Status pin for verification of Camera/RF connection |
| 7 | DGND | Power | Ground return for signals on pin 3 through 6 and pin 8 |
| 8 | Equip Sync | Output | |
| 9 | Camera Power | Power | Power for the camera. Equal to the battery voltage, and is switched off when the system power supplies are shut down |
| 10 | AGND | Power | Ground return for camera power |
| 11 | Video In | Input | Video input from the camera |
| 12 | AGND | Power | Ground return for the camera video |

The Parallel Flash Memory (PFM) 1050 may be used to store executable code and the Serial Flash Memory (SFM) 1055 may provide Serial Port Interface SPI for data storage. The PFM 1050 may be implemented using, for example, Intel TE28F160B3TD70. The PFM 1050 is connected to the address and data bus. The PFM may contain 512K words to map to an executable code space (PS) of the DSP 1020. A user-selectable switch (not shown) may be provided to enable or disable writing to the PFM 1050. The SFM 1055 may be implemented using, for example, STMicroelectronics M25P80. The SFM 1055 may contain 16 independently erasable sectors, with each sector containing, for example, 64K bytes.

The Real Time Clock 1060 may be battery backed up real time clock that is connected to the I2C bus. The Real Time Clock 1060 may be implemented using, for example, xicor X1226 that uses a 32.768 KHz crystal and draws 600 nA from a 48 mAH primary lithium cell to keep the clock running when the VPU 20 is powered off. The Real Time Clock 1060 may contain 512 bytes of flash EEPROM which may be programmed or read via the I2C bus.

The VIMC 1071 may be used to monitor the integrity status of the retinal stimulation system 1 by sampling and monitoring RF transmitter 1070's current and voltage. The RF transmitter 1070's current may be converted to voltage through a current sensitive resistor (not shown) of 100 mohm+/−2%. The voltage drop across the sensitive resister is amplified by a current shunt monitor to 0~2.0V of dynamic range. The voltage is buffered for AD converting. Vrf may also be sent through a resistor divider for AD converting. The AD converter may have resolution of 8 bits with a signal input range of 0~2V. The conversion accuracy of the AD converter for measuring RF transmitter current and Vrf may be, for example, ±3.6%.

Four external interrupt signals INT0 through INT3 may be input to the DSP 1020. The INT0 may have the highest priority and INT3 may have the lowest. The INT0 may be connected to the vertical sync output of the Video Preprocessor 1075 to signal the start of a new video frame. The INT1 may be connected to the Keypad interface of the IOP 1045 to signal when a key is depressed or released. The INT2 may be optional. The INT3 may be connected to signal ITRDY of the VPDI 1025.

Port 816 of FIGS. 11A-E is an Omnetics Connector that is used to connect the VPU 20 to the laptop 10 though the Communication Adapter (CA) 40 of FIG. 9. The Omnetics Connector may have 10 pins (identified in Table 13 below).

TABLE 13

Omnetics Connector Pin Definition

| Pin Name | Type | Function |
|---|---|---|
| 1 Transmit Data | Output | Transmit data to CA 40 |
| 2 Vcc | Input | +3.3 V for power to VPU side of CA opto-isolators |
| 3 Ground | Power | Ground connection to CA |
| 4 DataCLK | Output | Data clock from CA |
| 5 Receive Data | Output | Received data from CA |
| 6 N/C | Input | No connection |
| 7 FSR | Input | Frame Sync for receive data from CA |
| 8 Connect Verify | | Line to verify connection of the CA (low = connected, float = not connected) |
| 9 N/C | | No connection |
| 10 N/C | | No connection |

Keypad Connector is a 14-conducter flat connector for in-system keypad and LED connection.

The following are examples of Development Connectors according to one exemplary embodiment of the present application. A Programmable Logic Download Connector is a development connector for downloading the .jed file from Xilinx WebPack to on-board CPLD. The Programmable Logic Download Connector is compliant to JTAG, which is the commonly used acronym for the Boundary Scan Test (BST) feature defined for integrated circuits by IEEE Standard 1149.1. This standard defines input/output pins, logic control functions, and commands that facilitate both board and device level testing without the use of specialized test equipment. A DSP JTAG Connector is a development connector for linking the digital board to the DSP 1020 development system—Code Composer Studio. The DSP JTAG Connector is compliant to IEEE standard 1149.1. A Equipment Sync is a signal that is available through the Camera/RF connector port 815. The Equipment Sync provides a pulse (width 1 ms, positive going and 3.3V amplitude) to indicate that the first 16-bit word of a 1024 bit packet is being output by the forward telemetry logic.

The power button 805 of FIG. 12 may be used for turning the VPU 20 on/off. In one exemplary embodiment, the power button 805 may be depressed for a predetermined amount of time (for example 1.6±0.2 seconds) before the VPU 20 actually powers up. In another exemplary embodiment, the power button 805 may be depressed for another predetermined amount of time (for example 1.6±0.2 seconds) before the VPU 20 actually powers down.

Figures 1, 14:
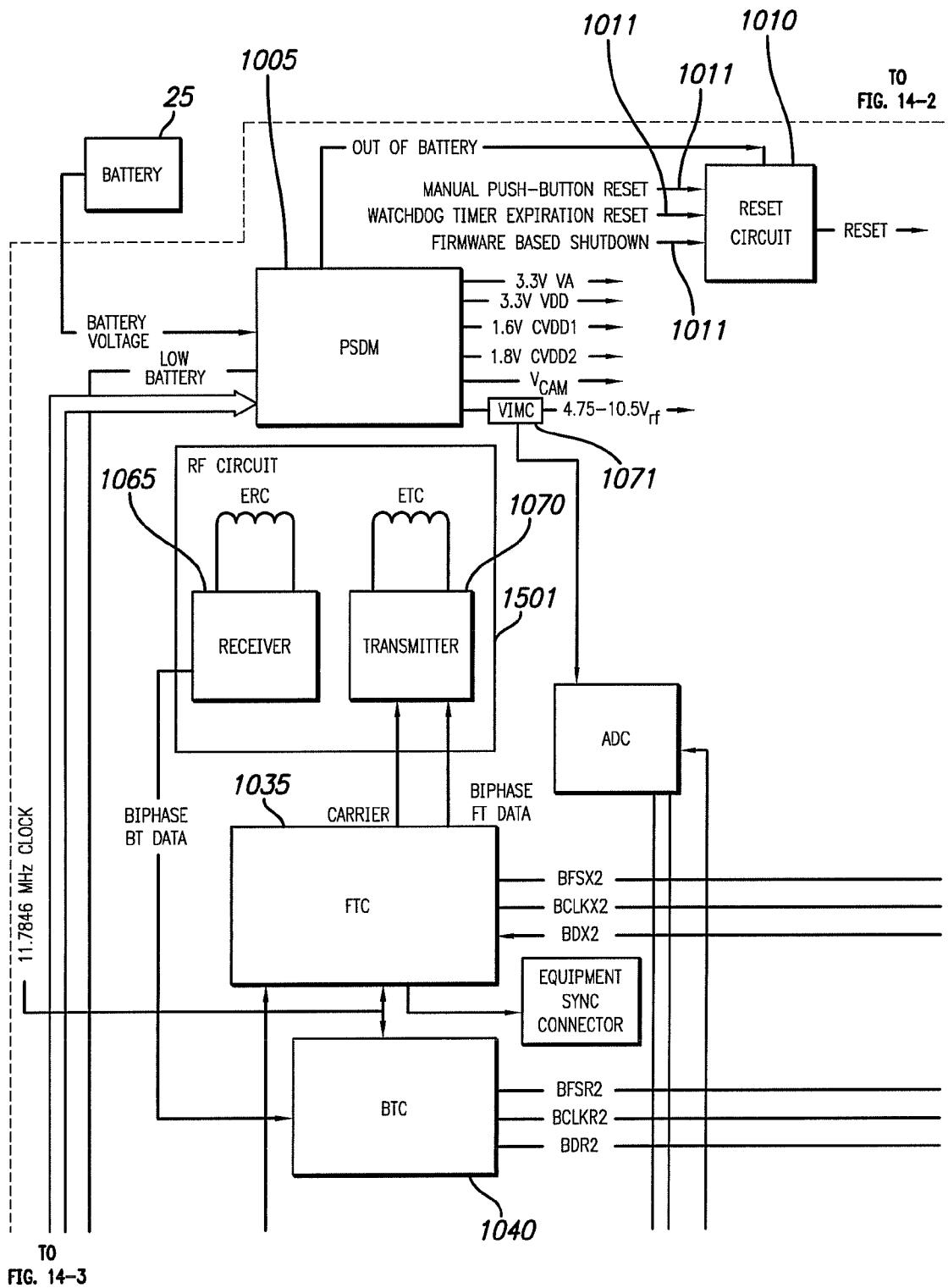
Figures 2, 14:
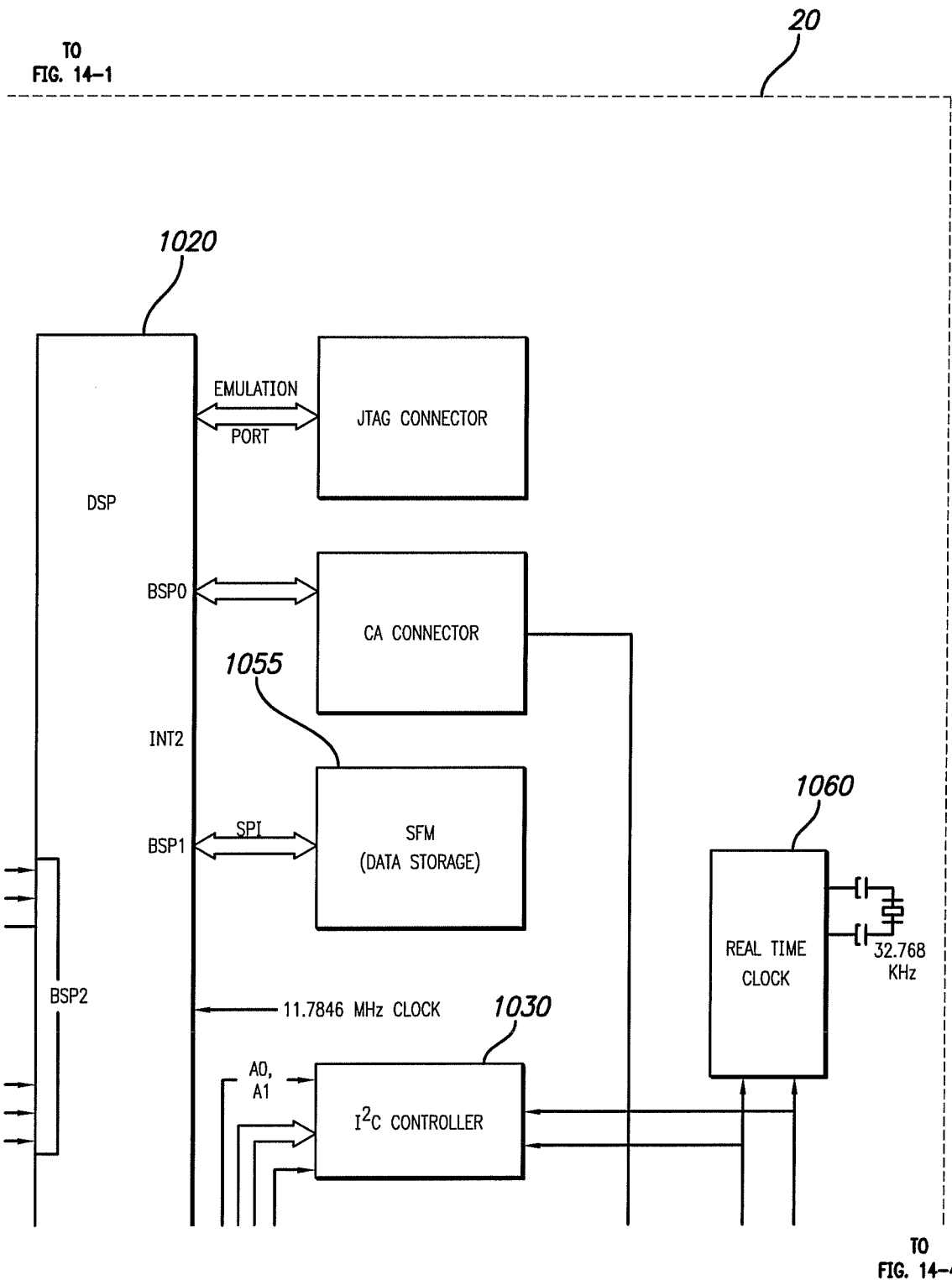
Figures 3, 14:
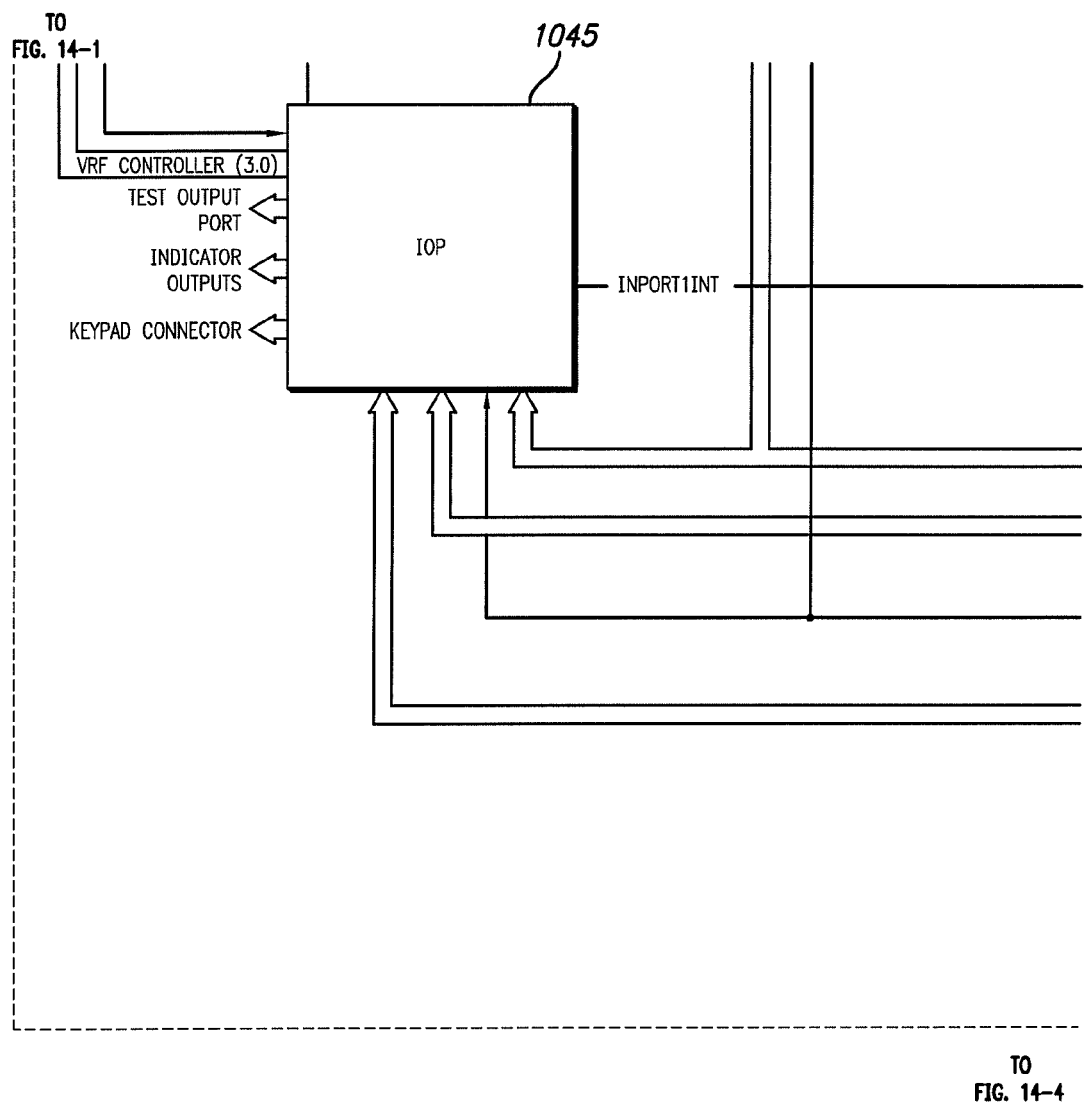
Figures 4, 14:
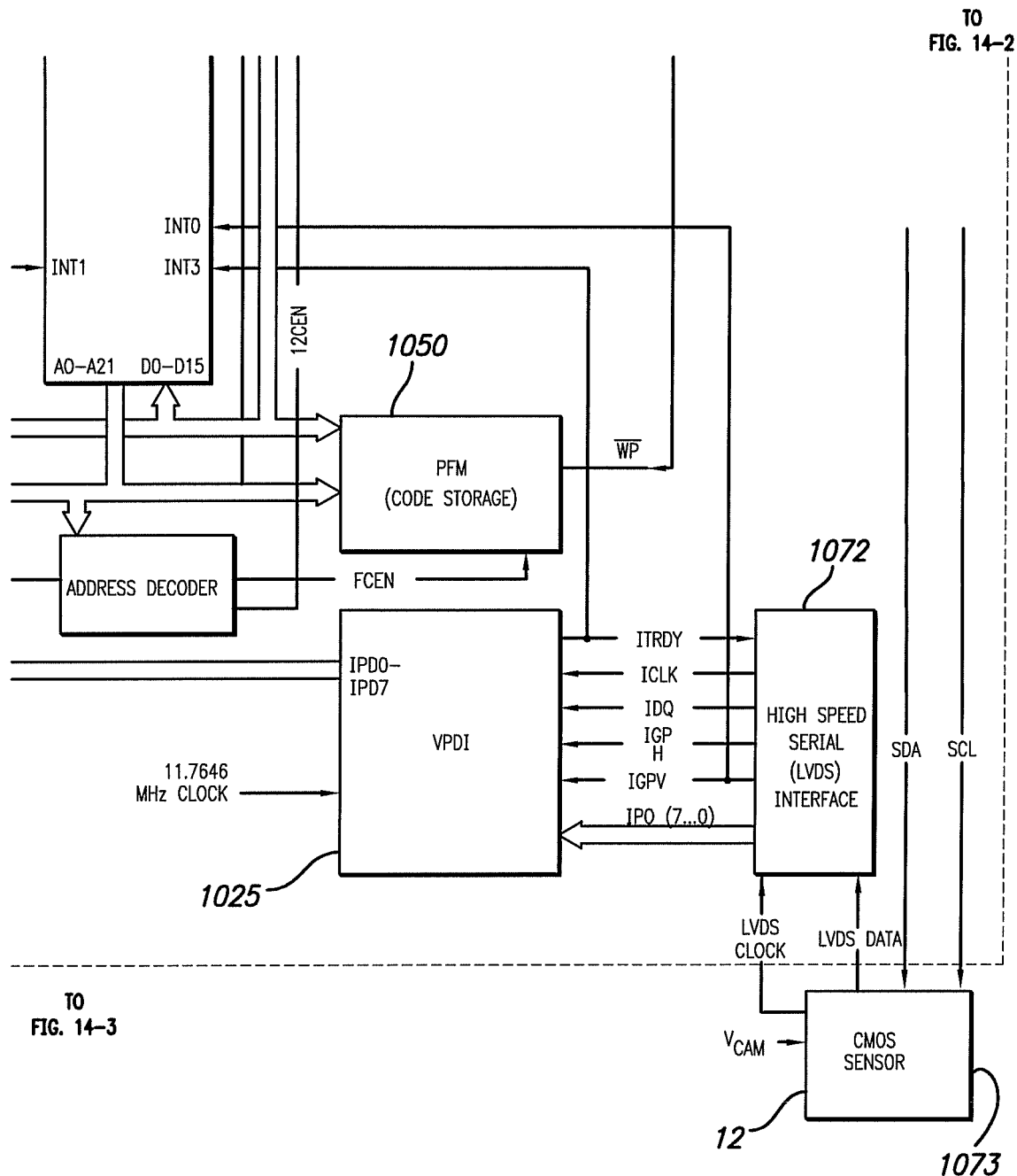

In one exemplary embodiment, a CMOS sensor 1073 that provides digital output may be used instead of the camera 12 as shown in FIGS. 14-1 to 14-4. The CMOS sensor 1073 may have within it, or be connected to a high-speed digital serial transmitter circuit such as one using the Low Voltage Differential Signal (LVDS) protocol. This serial data may be passed through the multi-conductor cable to an LVDS receiver 1072, which would be used in place of the video decoder circuit 1075. The receiver 1072 may perform serial-to-parallel conversion of the video data and thus provide the digital video stream to the VDPI circuit 1025. This embodiment may allow for elimination of the video decoder and may allow better control of the CMOS sensor 1073 via the programmable registers available within CMOS sensor 1073.

Due to the nature of the video data being processed, it may be advantageous to use a digital signal processor (DSP) 1020 for micro-controller. DSPs 1020 are more adept at applying digital filtering algorithms to the incoming video frames. For functions such as real-time control of the voltage to the RF circuit 1501 or handling the user interface, however, it is easier to program a general-purpose micro-controller (such as the ARM). It may be possible to use a so-called "dual core" device containing both an ARM (or other general purpose micro-controller) and a DSP. Each processor may be assigned to handle the functions they best serve. To save space, it may be possible to select a micro-controller that has the VDPI 1025 circuit built into it.

The following concepts are supported by the present application:

Concept 1. A visual prosthesis apparatus comprising:
    a video capture device for capturing a video image;
    a video processing unit associated with the video capture device, the video processing unit configured to convert the video image to stimulation patterns; and
    a retinal stimulation system configured to stimulate neural tissue in a subject's eye based on the stimulation patterns, wherein the video processing unit is configured to be powered on after a first time interval upon activation of a power button, wherein the video processing unit is configured to be powered off after a second time interval upon activation of a power button.

Concept 2. The visual prosthesis apparatus of Concept 1, wherein the first time interval is about 1.6 seconds.

Concept 3. The visual prosthesis apparatus of Concept 1 or 2, wherein the second time interval is about 1.6 seconds.

Concept 4. A visual prosthesis apparatus comprising:
- a video capture device for capturing a video image;
- a video processing unit associated with the video capture device, the video processing unit comprising
  - a video processor for converting the video image to a digital video stream;
  - a memory for storing the digital video stream;
  - a video preprocessor data interface for forming stimulation patterns based on the stored digital video stream; and
- a retinal stimulation system configured to stimulate neural tissue in a subject's eye based on the stimulation patterns.

Concept 5. The visual prosthesis apparatus of Concept 4, wherein the video processing unit further comprises a power supply distribution and monitoring circuit for generating appropriate voltages and adjusting power level of the stimulation patterns transmitted to the retinal stimulation system.

Concept 6. The visual prosthesis apparatus of Concept 5, wherein the power supply distribution and monitoring circuit is configured to turn off the video processing unit if the power from a battery providing energy to the video processing unit drops below a predetermined level.

Concept 7. The visual prosthesis apparatus of Concept 6, wherein the predetermined level is about 6.75 volts.

Concept 8. The visual prosthesis apparatus of any one of Concepts 4-7, wherein the video processing unit further comprises a reset circuit for resetting the video processing unit.

Concept 9. The visual prosthesis apparatus of Concept 8, wherein the reset circuit resets the video processing unit based on manual push-button reset, watchdog timer expiration or firmware based shutdown.

Concept 10. The visual prosthesis apparatus of any one of Concepts 4-9, wherein the video processing unit further comprises a digital signal processor for communicating with the video processor, the memory and the video preprocessor data interface.

Concept 11. The visual prosthesis apparatus of Concept 10, wherein the video processing unit further comprises a system main clock for the digital signal processor.

Concept 12. The visual prosthesis apparatus of any one of Concepts 4-11, wherein the video processor comprises:
- a video decoder for converting the video image into a high-resolution digitized image; and
- a video scaler for scaling down the high-resolution digitized image to the digital video stream.

Concept 13. The visual prosthesis apparatus of Concept 12, wherein the video decoder comprises:
- an analog input processing circuit;
- a chrominance and luminance processing circuit; and
- a brightness contrast and saturation control circuit.

Concept 14. The visual prosthesis apparatus of Concept 12 or 13, wherein the video scaler comprises;
- an acquisition control circuit;
- a pre-scaler circuit;
- a brightness contrast and saturation control circuit; and
- line buffer and output interface.

Concept 15. The visual prosthesis apparatus of Concept 10, wherein the video processor comprises:
- an $I^2C$ protocol controller configured to convert parallel bus interface of the digital signal processor to $I^2C$ protocol bus or vice versa.

Concept 16. The visual prosthesis apparatus of any one of Concepts 4-15, wherein the video processor comprises:
- a forward telemetry controller forming a forward telemetry frame for the retinal stimulation system; and
- a back telemetry controller decoding backward telemetry frame from the retinal stimulation system.

Concept 17. The visual prosthesis apparatus of any one of Concepts 4-16, wherein the video processor comprises:
- a parallel flash memory to store executable code; and
- a serial flash memory to store data.

Concept 18. The visual prosthesis apparatus of any one of Concepts 4-17, wherein the video processor comprises:
- a voltage and current monitoring circuit configured to monitor the integrity status of the retinal stimulation system by sampling and monitoring current and voltage of an RF transmitter.

Concept 19. The visual prosthesis apparatus of any one of Concepts 4-18, wherein the video capturing device is a video camera.

Concept 20. The visual prosthesis apparatus of any one of Concepts 4-19, wherein the video capturing device is a CMOS sensor.

Concept 21. The visual prosthesis apparatus of Concept 20, wherein the video processor comprises a high-speed digital serial transmitter circuit associated with the CMOS sensor.

Concept 22. The visual prosthesis apparatus of any one of Concepts 4-21, wherein the video processor comprises:
- a digital signal processor configured to apply digital filtering algorithms to the video image; and
- a general-purpose micro-controller configured to provide real-time control of voltage to an RF circuit or configured to control a user interface.

Concept 23. A video processing unit configured to convert a video image to stimulation patterns for stimulating neural tissue in a subject's eye and comprising a power button, wherein the video processing unit is configured to be powered on after a first time interval upon activation of a power button, wherein the video processing unit is configured to be powered off after a second time interval upon activation of a power button.

Concept 24. The video processing unit of Concept 23, wherein the first time interval is about 1.6 seconds.

Concept 25. The video processing unit of Concept 23 or 24, wherein the second time interval is about 1.6 seconds.

Concept 26. A video processing unit configured to convert a video image to stimulation patterns for stimulating neural tissue in a subject's eye, the video processing unit comprising
- a video processor for converting a video image to a digital video stream;
- a memory for storing the digital video stream; and
- a video preprocessor data interface for forming stimulation patterns based on the stored digital video stream.

Concept 27. The video processing unit of Concept 26, wherein the video processing unit further comprises a power supply distribution and monitoring circuit for generating appropriate voltages and adjusting power level of the stimulation patterns transmitted to a retinal stimulation system.

Concept 28. The video processing unit of Concept 27, wherein the power supply distribution and monitoring circuit is configured to turn off the video processing unit if the power from a battery providing energy to the video processing unit drops below a predetermined level.

Concept 29. The video processing unit of Concept 28, wherein the predetermined level is about 6.75 volts.

Concept 30. The video processing unit of any one of Concepts 26-29, wherein the video processing unit further comprises a reset circuit for resetting the video processing unit.

Concept 31. The video processing unit of Concept 30, wherein the reset circuit resets the video processing unit based on manual push-button reset, watchdog timer expiration or firmware based shutdown.

Concept 32. The video processing unit of any one of Concepts 26-31, wherein the video processing unit further comprises a digital signal processor for communicating with the video processor, the memory and the video preprocessor data interface.

Concept 33. The video processing unit of Concept 32, wherein the video processing unit further comprises a system main clock for the digital signal processor.

Concept 34. The video processing unit of any one of Concepts 26-33, wherein the video processor comprises:
  a video decoder for converting the video image into a high-resolution digitized image; and
  a video scaler for scaling down the high-resolution digitized image to the digital video stream.

Concept 35. The video processing unit of Concept 34, wherein the video decoder comprises:
  an analog input processing circuit;
  a chrominance and luminance processing circuit; and
  a brightness contrast and saturation control circuit.

Concept 36. The video processing unit of Concept 34 or 35, wherein the video scaler comprises;
  an acquisition control circuit;
  a pre-scaler circuit;
  a brightness contrast and saturation control circuit; and
  line buffer and output interface.

Concept 37. The video processing unit of Concept 32, wherein the video processor comprises:
  an I$^2$C protocol controller configured to convert parallel bus interface of the digital signal processor to I$^2$C protocol bus or vice versa.

Concept 38. The video processing unit of any one of Concepts 26-37, wherein the video processor comprises:
  a forward telemetry controller forming a forward telemetry frame for a retinal stimulation system; and
  a back telemetry controller decoding backward telemetry frame from the retinal stimulation system.

Concept 39. The video processing unit of any one of Concepts 26-38, wherein the video processor comprises:
  a parallel flash memory to store executable code; and
  a serial flash memory to store data.

Concept 40. The video processing unit of any one of Concepts 26-39, wherein the video processor comprises:
  a voltage and current monitoring circuit configured to monitor the integrity status of a retinal stimulation system by sampling and monitoring current and voltage of an RF transmitter.

Concept 41. The video processing unit of any one of Concepts 26-40, wherein the video processor comprises:
  a digital signal processor configured to apply digital filtering algorithms to the video image; and
  a general-purpose micro-controller configured to provide real-time control of voltage to an RF circuit or configured to control a user interface.

Concept 42. A method for providing artificial vision, the method comprising:
  powering a video processing unit a first amount of time after a power button is activated;
  capturing a video image;
  converting the video image to stimulation patterns using the video processing unit; and
  stimulating neural tissue in a subject's eye based on the stimulation patterns.

Concept 43. The method of Concept 42, further comprising:
  Powering off a video processing unit a second amount of time after a power button is activated.

Concept 44. The method of Concept 42 or 43, wherein the first amount of time is about 1.6 seconds.

Concept 45. The method of Concept 43 or 44, wherein the second amount of time is about 1.6 seconds.

Concept 46. A method for providing artificial vision, the method comprising:
  capturing a video image;
  converting the video image to a digital video stream;
  storing the digital video stream;
  forming stimulation patterns based on the stored digital video stream; and
  stimulating neural tissue in a subject's eye based on the stimulation patterns.

Concept 47. The method of Concept 46, further comprising:
  generating appropriate voltages and adjusting power level of the stimulation patterns.

Concept 48. The method of Concept 46 or 47, further comprising turning off power if the power from a battery drops below a predetermined level.

Concept 49. The method of Concept 48, wherein the predetermined level is about 6.75 volts.

Concept 50. The method of any one of Concepts 46-49, further comprising:
  converting the video image into a high-resolution digitized image; and
  scaling down the high-resolution digitized image to the digital video stream.

Concept 51. The method of any one of Concepts 46-50, further comprising:
  forming a forward telemetry frame for stimulating neural tissue in the subject's eye.

Concept 52. The method of any one of Concepts 46-51, further comprising:
  storing executable code in parallel flash memory; and
  storing data in a serial flash memory.

Concept 53. A visual prosthesis apparatus comprising:
  a video capture device for capturing a video image;
  a video processing unit associated with the video capture device, the video processing unit configured to convert the video image to stimulation patterns; and
  a retinal stimulation system configured to stimulate neural tissue in a subject's eye based on the stimulation patterns,
  wherein the video processing unit is configured to be powered on after a first time interval upon activation of a power button,
  wherein the video processing unit is configured to be powered off after a second time interval upon activation of a power button,
  wherein the video processing unit is disposed on a visor.

Concept 54. The visual prosthesis apparatus of Concept 53, wherein the first time interval is about 1.6 seconds.

Concept 55. The visual prosthesis apparatus of Concept 53 or 54, wherein the second time interval is about 1.6 seconds.

Concept 56. A visual prosthesis apparatus comprising:
  a video capture device for capturing a video image;
  a video processing unit associated with the video capture device, the video processing unit comprising
    a video processor for converting the video image to a digital video stream;

a memory for storing the digital video stream;
a video preprocessor data interface for forming stimulation patterns based on the stored digital video stream; and
a retinal stimulation system configured to stimulate neural tissue in a subject's eye based on the stimulation patterns,
wherein the video processing unit is disposed on a visor.

Concept 57. The visual prosthesis apparatus of Concept 56, wherein the video capturing device is a video camera.

Concept 58. The visual prosthesis apparatus of Concept 56, wherein the video capturing device is a CMOS sensor.

Concept 59. The visual prosthesis apparatus of Concept 58, wherein the video processor comprises a high-speed digital serial transmitter circuit associated with the CMOS sensor.

Concept 60. A video processing unit configured to convert a video image to stimulation patterns for stimulating neural tissue in a subject's eye and comprising a power button, wherein the video processing unit is configured to be powered on after a first time interval upon activation of a power button, wherein the video processing unit is configured to be powered off after a second time interval upon activation of a power button, wherein the video processing unit is disposed on a visor.

As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

Accordingly, what has been shown is an improved visual prosthesis, improved method of stimulating neural tissue and an improved method for controlling a visual prosthesis. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. A video processing unit configured for communication with an implantable visual prosthesis and further configured to convert a video image to stimulation patterns for stimulating visual neural tissue and comprising a power button and other buttons and an indicator light, wherein the video processing unit is configured to be powered on and provide a first user notification to a patient after the power button is continuously activated for a first predetermined time interval, wherein the video processing unit is configured to be powered off and provide a second user notification to the user different from said first notification after the power button is continuously activated for a second predetermined time interval upon activation of the power button, and wherein the power button is differently shaped than the other buttons, and wherein the indicator light provides different signals to indicate the first predetermined interval, the second predetermined interval, a normal operation mode and an error mode, wherein when the error mode is activated the video processing unit will shut down automatically.

2. The video processing unit of claim 1, wherein the first predetermined time interval is about 1.6 seconds.

3. The video processing unit of claim 1, wherein the second predetermined time interval is about 1.6 seconds.

4. The video processing unit according to claim 1, wherein the user notification is an audible signal.

5. The video processing unit according to claim 4, wherein the audible signal comprises a beep.

6. A method for providing artificial vision for use with an implantable visual prosthesis configured to communicate with a video processing unit, the method comprising: identifying a power button on the video processing unit by identifying a different outermost surface parallel to the direction of activation, powering on the video processing unit and providing a first user notification to a patient after the power button is continuously activated for a first predetermined amount of time, capturing a video image; converting the video image to stimulation patterns for the implantable visual prosthesis using the video processing unit, stimulating neural tissue in the patient's eye based on the stimulation patterns, and providing a second user notification to the patient, different from the first notification, to indicate an error mode wherein when the error mode is activated the video processing unit will shut down automatically.

7. The method of claim 6, further comprising:
powering off a video processing unit after the power button is continuously activated for a second predetermined amount of time.

8. The method of claim 6, wherein the first amount of time is about 1.6 seconds.

9. The method of claim 7, wherein the second amount of time is about 1.6 seconds.

10. A video processing unit configured for communication with an implantable visual prosthesis and further configured to convert a video image to stimulation patterns for stimulating neural tissue in a subjects eye and comprising a power button and other buttons, wherein the video processing unit is configured to be powered on and provide a first audible signal after the power button is continuously activated for a first predetermined time interval, wherein the video processing unit is configured to be powered off and provide a second audible signal different from said first audible signal after the power button is continuously activated for a second predetermined time interval, wherein the video processing unit is disposed on a visor and wherein the power button is differently shaped than the other buttons and wherein the indicator light provides different signals to indicate the first predetermined interval, the second predetermined interval, a normal operation mode and an error mode, wherein when the error mode is activated the video processing unit will shut down automatically.

11. The video processing unit according to claim 1, wherein the power button is circular, and other buttons are shaped other than circular.

* * * * *